United States Patent
Al Alawi et al.

(10) Patent No.: US 9,452,155 B2
(45) Date of Patent: *Sep. 27, 2016

(54) INJECTABLE ANTIBIOTIC FORMULATIONS AND THEIR METHODS OF USE

(71) Applicant: BAYER NEW ZEALAND LTD, Hamilton (NZ)

(72) Inventors: Fadil Al Alawi, Auckland (NZ); Karthigeyan Nanjan, Hamilton (NZ)

(73) Assignee: BAYER NEW ZEALAND LTD, Hamilton (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 14/415,954

(22) PCT Filed: Jul. 16, 2013

(86) PCT No.: PCT/NZ2013/000124
§ 371 (c)(1),
(2) Date: Jan. 20, 2015

(87) PCT Pub. No.: WO2014/014364
PCT Pub. Date: Jan. 23, 2014

(65) Prior Publication Data
US 2015/0150854 A1    Jun. 4, 2015

(30) Foreign Application Priority Data

Jul. 17, 2012 (NZ) .................................. 601299
May 3, 2013 (NZ) .................................. 610175
Jul. 12, 2013 (NZ) .................................. 613138
Jul. 15, 2013 (NZ) .................................. 613240

(51) Int. Cl.
| | |
|---|---|
| A61K 9/14 | (2006.01) |
| A61K 31/43 | (2006.01) |
| A61K 47/14 | (2006.01) |
| A61K 9/10 | (2006.01) |
| A61K 9/00 | (2006.01) |
| A61K 47/26 | (2006.01) |

(52) U.S. Cl.
CPC ............ *A61K 31/43* (2013.01); *A61K 9/0019* (2013.01); *A61K 9/10* (2013.01); *A61K 47/14* (2013.01); *A61K 47/26* (2013.01)

(58) Field of Classification Search
None
See application file for complete search history.

(56) References Cited

U.S. PATENT DOCUMENTS

| | | |
|---|---|---|
| 4,446,144 A | 5/1984 | von Daehne |
| 4,594,246 A | 6/1986 | von Daehne |
| 4,672,114 A | 6/1987 | von Daehne |
| 4,831,025 A | 5/1989 | Godtfredsen et al. |
| 4,882,325 A | 11/1989 | Godtfredsen et al. |
| 2006/0142234 A1 | 6/2006 | Chen et al. |
| 2010/0226997 A1* | 9/2010 | Bowman ............... A61K 9/0048 424/501 |

FOREIGN PATENT DOCUMENTS

| | | |
|---|---|---|
| CN | 1517090 A | 8/2004 |
| GB | 2084572 A | 4/1982 |
| GB | 2087236 A | 5/1982 |
| WO | 2013095166 A1 | 6/2013 |

OTHER PUBLICATIONS

Patel, Rajesh M., International Journal of Current Pharmaceutical Research, 2010, 2(3):4-20.
Water-Insoluble Drug Formulation 2008 (Ring Liu(ed)).
Summary of Product Characteristics: Ubro Red Dry Cow Intramammary Suspension Jun. 2010 (Boehringer Ingelheim Ltd).
Handbook of Powder Technology—Dispersing Powders in Liquids 1988(R.D. Nelson).
Edwards, S.J. Penicillin Levels in the Milk Following Intramuscular Injection.

* cited by examiner

*Primary Examiner* — Susan Tran
(74) *Attorney, Agent, or Firm* — Yonggang Ji

(57) ABSTRACT

This invention relates to a composition, including penethamate (PNT) or a pharmaceutical equivalent thereof; and triacetin.

23 Claims, 16 Drawing Sheets

INJECTABLE ANTIBIOTIC FORMULATIONS AND THEIR METHODS OF USE

TECHNICAL FIELD

The present invention relates to injectable antibiotic formulations and their methods of use, and particularly, but not specifically to the treatment or prevention of mastitis in lactating animals.

BACKGROUND ART

Microbial infections in animals, such as mastitis in dairy cows, are typically treated or prevented during the lactation period by, intramammary (IMM) infusion, intramuscular (IM) or subcutaneous (SC) injection.

Typically, antibiotics such as penicillins or prodrugs of benzylpenicillin (BP) such as penethemate (PNT) have been used as actives of choice to treat bovine mastitis. PNT is the diethylaminoethyl ester of benzylpenicillin. In formulations intended for veterinary use PNT is incorporated as the hydroiodide (HI). PNT HI is used in intramammary products during lactation (UBRO YELLOW™, Boehringer Ingelheim) and during the dry-off period (UBRO RED™, Boehringer Ingelheim), as well as an injectable suspension during lactation period (Mamyzin™, Boehringer Ingelheim and Penethaject™, Bayer Animal Health) for treatment of mastitis in cows.

PNT is a prodrug from which benzylpenicillin and diethylaminoethanol are released by hydrolysis. Antimicrobial activity of the compound is exclusively related to benzylpenicillin. The maximum residue limit (MRL) for milk in bovine in e.g. Europe and New Zealand is 4 µg/kg (EMEA, BP).

As a prodrug of benzylpenicillin, penethamate hydroiodide is effective in treating mastitis as a result of its particular pharmacokinetics. After intramuscular administration, penethamate hydroiodide is absorbed from the site of injection and on entering the blood partially dissociates by hydrolysis into benzylpenicillin and diethylaminoethanol. At blood pH (7.2), an equilibrium is established wherein 91.8% of the active drug is present in its hydrolysed form (benzylpenicillin) with the remainder being penethamate. The equilibrium is maintained by re-association of benzylpenicillin and diethylaminoethanol. Peak serum levels (measured as dissociated penicillin G) are rapidly reached, 3.76 hours after injection (Friton 2003).

The un-disassociated form of penethamate easily passes over the blood-milk barrier due to the pH gradient present between milk (pH 6.6-6.8) and plasma (pH 7.2) and its weakly basic state (pKa=8.4). The lipophilic nature of penethamate further facilitates its passage across the lipoproteineic blood-milk barrier. Penethamate starts to dissociate as it passes over the blood-milk barrier and this continues during diffusion of the drug throughout the udder, releasing benzylpenicillin. The benzylpenicillin is rapidly ionised in the udder (pKa=2.8), as a result of the lower pH of milk, trapping the active within the udder in increasing concentrations.

Current PNT products available on the market for intramuscular (IM) or sub-cutaneous (SC) injection, are in the form of a powder for reconstitution into solution or suspension with sterile water at the time of use (e.g. Mamyzin™ Boehringer Ingelheim or Penethaject™ Bayer Animal Health). Typical dosages of these products include three daily doses of 5 g of PNT, or one dose of 10 g followed by a 5 g dose the next day.

The use of an aqueous vehicle allows for the PNT to dissolve quickly at the injection site and thus be rapidly absorbed. Especially desirable properties for treating mastitis during the lactation period include rapid absorption of the active, effective therapeutic action, and a short withhold period. The ability of penethamate to cross the blood/milk barrier and concentrate in the udder, provides effective therapeutic action and a sufficiently short withhold period.

Despite their effectiveness as therapeutic actives, a disadvantage of currently available compositions as injections containing penicillin or PNT is their limited shelf-life (often only 2-3 days) once reconstituted into an aqueous solution from a powder. This is inconvenient to the user, who must reconstitute the powder into a liquid form, such as by drawing out a sterile aqueous vehicle from one vial, dispense the liquid into a second vial containing the powder and mix until a solution or homogeneous suspension is formed. Once the product is reconstituted it must be used within the limited period of stability, or it must be discarded.

Currently, there is no ready to use IM/SC injectable formulation of PNT to treat bovine mastitis or other diseases available on the market. A significant problem in developing a ready to use injectable formulation is the lack of storage stability of PNT in aqueous vehicles. The use of non-aqueous vehicles has been avoided for PNT formulations, since oil vehicles in particular typically provide a much slower release of the active after IM/SC injection. A slow release of the active would extend the withhold period for lactating cows, which is especially undesirable and would likely prevent commercialisation of the product.

The published patent document U.S. Pat. No. 4,446,144 mentions that PNT can be used in suspensions or solutions in suitable vehicle which can be made of an aqueous or oily base. Non-aqueous vehicles are indicated as providing better stability. The formulations described in U.S. Pat. No. 4,446,144 are for parenteral use, e.g. injections given as an aqueous solution or suspension. No mention is made of the desirability of obtaining fast-release of the active or bioequivalence with aqueous formulations.

There has been limited research in formulating a PNT composition for a IM/SC injection using a non-aqueous vehicle. Edwards, S. J. (1964), The Veterinary Record, Vol. 78, No. 17, 583-5, documents a study of penicillin levels in milk following intramuscular injection.

The prior art products requiring reconstitution of PNT into an aqueous vehicle provide a compromise, with the advantage of the rapid absorption of the active when administered, with the disadvantage of the limited storage stability of the reconstituted composition.

There has been a long felt need for a PNT composition that is ready to use, has good storage stability, and rapid release of the active.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

Throughout this specification, the word "comprise", or variations thereof such as "comprises" or "comprising", will be understood to imply the inclusion of a stated element, integer or step, or group of elements integers or steps, but not the exclusion of any other element, integer or step, or group of elements, integers or steps.

Further aspects and advantages of the present invention will become apparent from the ensuing description which is given by way of example only.

DISCLOSURE OF INVENTION

According to one aspect of the present invention there is provided a composition, including penethamate (PNT) or a pharmaceutical equivalent thereof; and triacetin.

Preferably the viscosity of the composition is below 3000 mPas at a temperature of 20° C. and shear rate of 1/s measured with a cup cylinder method.

Triacetin is an oily vehicle (5% solubility in water) with a viscosity of approximately 23 mPas at 20° C. and a density of 1.16 g/cm$^3$ Preferably the penethamate (PNT) or pharmaceutical equivalent thereof comprises 55% w/v or less of the composition.

Preferably the composition includes at least one anticaking agent.

According to a further aspect of the present invention there is provided a composition, the The inventors have formulated PNT compositions that overcome many of the disadvantages of the prior art PNT composition.

The present invention presents a ready to use injectable composition of PNT that can provide similar bioavailability or bioequivalence to aqueous based injectables.

The compositions of the invention advantageously avoid hydrolysis of the active by using Triacetin. Initial studies have shown substantially no degradation of the PNT active or other stability issues even after storage over 180 days at 30° C.

This is a clear advantage over prior art formulations such as Penethaject™, which has a shelf life of approximately only two days after reconstitution and storage at 25° C. (or just one week when stored at 2-8° C.). Users may be able to store the composition of the present invention in a ready-to-use liquid preparation, for example in a pre-prepared syringe. In large dairy farms, and particularly during the milking season, this invention presents a significant contribution to the art over other compositions currently used in the industry.

Various oil based compositions are previously known in the art for delivering antibiotics as an injectable liquid. Oil is used to avoid hydrolysis (i.e. degradation and hence poor stability) of the active, that may result from the use of an aqueous base. However, the use of oils have been used to provide a sustained release profile of the active over a relatively long period of time.

The present invention was surprisingly provides a fast release of the PNT and a short withholding period (WHP). These advantageous features are both provided by the aqueous based composition Penethaject™ for treatment/prevention of mastitis during the lactation period. This is contrary to what was expected.

Previously available oily injectable formulations have a significantly longer sustained release profiles.

Therefore, the present invention may have particular application to treatment or prevention of conditions such as mastitis in lactating animals, where a fast release, short persistency and short WHP is desired.

Additionally, the use of the present invention was also surprisingly found to have a bioavailability profile similar and potentially better than the prior art aqueous based formulations such as Penethaject™. The prior art has focused on provision of PNT formulations in aqueous based systems because of the required bioavailability. While it has also been expected that an oily formulation will result in slower release and longer withhold times.

Therefore, the inventors have identified a solution to address the current problem of poor stability and shelf life of PNT compositions suitable or SC/IM injection for treatment of mastitis. The present invention also provides means for improving the WHP and bioavailability characteristics compared with other veterinary compositions typically used for treatment or prevention of mastitis during an animal's lactation period.

Further while oily vehicles have been used with benzyl penicillin (Penicillin G) and/or procaine pencillin (see Chinese Patent No. 1517090) tests by the inventors have shown these to be chemically unstable on storage. Thus the long term stability of PNT with triacetin (or other oily vehicles) is highly unexpected.

In particular, the inventors trials have determined that when procaine penicillin is substituted for the penethamate in the preferred formulation of the present invention, the resulting composition is chemically unstable. After one month in accelerated stability the components of the composition appeared to degrade rapidly with a resulting colour change from an off-white to a dark yellow with dark brown sludge forming. The degradation components appeared to include a gas, resulting in the container swelling from the resultant pressure. Accordingly, the formulations described in CN 1517090 are not known to be storage stable.

The use of triacetin provided a storage stable formulation, both chemically and physically. The triacetin alone advantageously prevented the caking issues of the other oily vehicle formulations. The addition of the surface active agents further improved the re-suspendability of the composition on storage.

The withhold time was found to be equivalent to that of a known but unstable product called Mamyzin, and it was bio-equivalent.

Throughout this specification, the term penethamate (PNT) should be taken as meaning the diethylaminoethyl ester prodrug of benzyl penicillin (BP). It is BP that is the antibacterial active agent relied on in the present invention, and as well known in the industry.

It has been found that triacetin gives the desired results with regards to a WHP and bioavailability profile comparable to currently available aqueous based penethamate compositions.

Preferably, the ratio of PNT to triacetin is between 1:1 to 1:4 w/v.

However, the composition of the present invention may also be used to treat other bacterial infections similar to those treated with Penthaject™ such as metritis, respiratory infections and footrot in cattle and horses.

A prior art document CN 101822637 discloses the use of ethyl oleate as the carrier for β-lactam antibiotics. The compositions include 2-5% of active, with suspending agents 2%, thickeners 0.1-3% and preservatives such as benzyl alcohol. The suspending agents include aluminium stearate, which would increase the viscosity, and the thickening agents are said to include Tween 80.

The present invention is distinguished from this document in that it uses specifically penethamate hydroiodide, which as an ester of a β-lactam may be expected to have different properties and carrier requirements. The amount of antibiotic is significantly different, since the minimum of 20% PNT in the current formulations poses different problems to the 2-5% of the prior art document. Triacetin is a far better vehicle, being suitable for injection and less likely to cause caking of the suspended PNT.

Preferably, the concentration of PNT in the composition is between 15%-55% w/v.

Most preferably, the concentration of PNT in the composition is between 20% to 35% w/v.

The inventors identified these preferred amounts of PNT in the composition may be sufficient to provide about 5 g of active to the animal in a given dosage. In previous studies, this amount of PNT which was identified to provide a therapeutic effect similar to Penethaject™.

Preferably, the particle diameter $d_{50}$ of the PNT is between 1-100 microns.

Most preferably, the particle diameter $d_{50}$ of the PNT is between 8-30 microns with 95%<50 microns This is the approximate particle size of the PNT in the currently available Penethaject™ formulation. This feature may be important to help provide or improve bioavailability profiles of the composition.

In a particularly preferred embodiment, the composition includes at least one excipient which prevents caking.

Surprisingly, the inclusion of an additional excipient such as certain surfactants can dramatically improve the physical stability of PNT non-aqueous suspensions. For example, polysorbate 80 works particularly well in a preferred embodiment.

Typically, suspensions are physically stabilized by adding a standard anti-caking agent or thickener such as colloidal silicon dioxide or aluminium stearate. While colloidal silicon dioxide should not be administered parenterally (Handbook of Pharmaceutical Excipients), aluminium stearate thickens the suspension which slows down the drug release from the vehicle. These agents do not deliver a practical solution to physically stabilise PNT suspensions.

It was found that triacetin is a vehicle that dramatically improves physical stability of PNT suspension but at the same time delivers satisfying chemical stability. This is surprising given that triacetin is partially soluble with water, (while still being considered an oily vehicle) which would be expected to lead to hydrolysis of the active.

On the other hand non-oily vehicles such as water and propylene glycol deliver good physical stability of PNT suspensions, but such PNT suspensions are only chemically stable for a few days (eg water based Mamyzin) or less than 2 months during storage for propylene glycol. Again, this does not deliver a practical solution for a ready to use PNT composition with acceptable shelf life.

Surprisingly, it was also found that oily vehicles such as ethyl oleate or medium chain triglycerides in combination with specific excipients improves the physical stability of PNT suspension without compromising on chemical stability.

Surprisingly, it was found that certain types of lecithin can dramatically improve the physical stability of PNT suspensions while other types of lecithin do not. For instance a practically insoluble (at room temperature) hydrogenated soybean lecithin in oily vehicle has a positive impact on the physical stability of PNT suspensions but a solubilized soybean lecithin in an oily vehicle does not.

It was also found that adding Span 80 to an triacetin consisting of a medium chain triglyceride and a hydrogenated soybean lecithin does not negatively impact on the physical stability of PNT suspensions, but can increase the bioavailability of the PNT.

However, it should be appreciated that a number of different surfactants may be substituted for the above ones, yet still provide a physically stable PNT suspension, without compromising on chemical stability which lead to the beneficial results as described herein. A person skilled in the art would be able to readily ascertain the ability of any particular surfactant to stabilise a suspension of PNT.

Further, the inclusion of a surfactant did not deleteriously affect the beneficial stability nor the short WHP of the composition.

Contrary to expectations and the typical properties of drug release from an oily vehicle, it was found that the PNT release from triacetin according to the present invention could be as quick, or even quicker as the control aqueous based formulations.

This fast release profile from an oily vehicle may be important as it allows quick absorption of PNT, and hence provides a fast therapeutic effect.

In preferred embodiments, the surfactant is hydrogenated soybean lecithin

This surfactant was shown to substantially improve the release of PNT from the oily base after administration (see Example 3 in the Best Modes section). Given the results exemplified herein, one skilled in the art would expect that a similar surfactant or surfactants to hydrogenated soybean lecithin for instance falling within the HLB range of 7-16, would also provide a similar beneficial effect to the current composition.

However Tween 80 has shown significantly better results when with triacetin as the vehicle. It works well as an anti-caking compound plus does not have thickening properties.

In preferred embodiments at least one preservative is included. For example, methyl paraben and propyl paraben or benzyl alcohol may be used as preservatives.

Benzyl/alcohol is preferred with triacetin based formulations as it mixes well with triacetin maintains its activity in oily vehicles as well as being suitable for injections.

For the usefulness of the product, the preservative is important since it allows the ready-to-use composition to be used on multiple occasions. A study was performed to test the stability and sterility of the present invention product after removal of a dose from the container:

In this study the penethamate suspension (in accordance with the preferred formulation), packed in 100 mL clear PET vials stored at room temperature were broached, using 10 mL sterile disposable syringe with 16 G hypodermic needle, each week for four weeks. On each occasion an appropriate amount of sample was removed and after day 28, the left over sample was analysed for physical, chemical and microbial characteristics. The results show that the penethamate suspension, remains physically and chemically stable after repeated broaching over a period of 28 days at room temperature.

Further the sterility of the samples was not compromised by repeated broaching after in-use stability trial period of 28 days.

Method of Treatment

According to another aspect of the present invention there is provided a method of treating an animal with a composition substantially as described herein for the treatment or prevention of a microbial infection, wherein the method includes intramuscular or subcutaneous injection of the composition to the animal in need thereof.

Preferably, the microbial infection is pre-clinical or clinical mastitis.

Preferably, the method of treatment includes a dosage regime of 5 g PNT per day repeated for approximately three days.

An alternative dosage regime may include delivery of 10 g PNT as a first dose on a first day, followed by a further dose of 5 g PNT on the second day. Such dosages are similar to that currently advised for Penthaject™.

According to another aspect of the present invention there is provided a use, in the manufacture of a composition as substantially described herein, for treating or prevent a microbial infection in an animal.

Method of Manufacture

According to a further aspect of the present invention there is provided a method of manufacturing the composition as substantially described above including the steps of:
  a) either (i) providing triacetin, or (ii) mixing triacetin and surfactant(s) in a container to form a homogenous mixture;
  b) dispersing the active agent in the triacetin or mixture Optionally, at least one preservative is added to the oily vehicle in step a).

Preferably, the oily vehicle of step a) is sterilized by filtration.

Preferably, step b) utilises high shear dispersion equipment.

An additional advantage of the composition's preferred low viscosity is beneficial to the manufacturing process.

Likewise, the lower viscosity allows for easier filling of containers, such as vials or syringes, following manufacturing of the composition.

Preferred the active agents are micronised. The use of micronized active agents can help prevent quick settling of the solids within the composition.

BRIEF DESCRIPTION OF DRAWINGS

Further aspects of the present invention will become apparent from the ensuing description which is given by way of example only and with reference to the accompanying drawings in which:

FIG. 7 Inhibitory substance concentration in milk following intramuscular administration of compositions OT11PNTRTU-f, and -h;

FIG. 8 Inhibitory substance concentration in milk following intramuscular administration of compositions OT11PNTRTU-i, and -j;

BEST MODES FOR CARRYING OUT THE INVENTION

Figure 1:
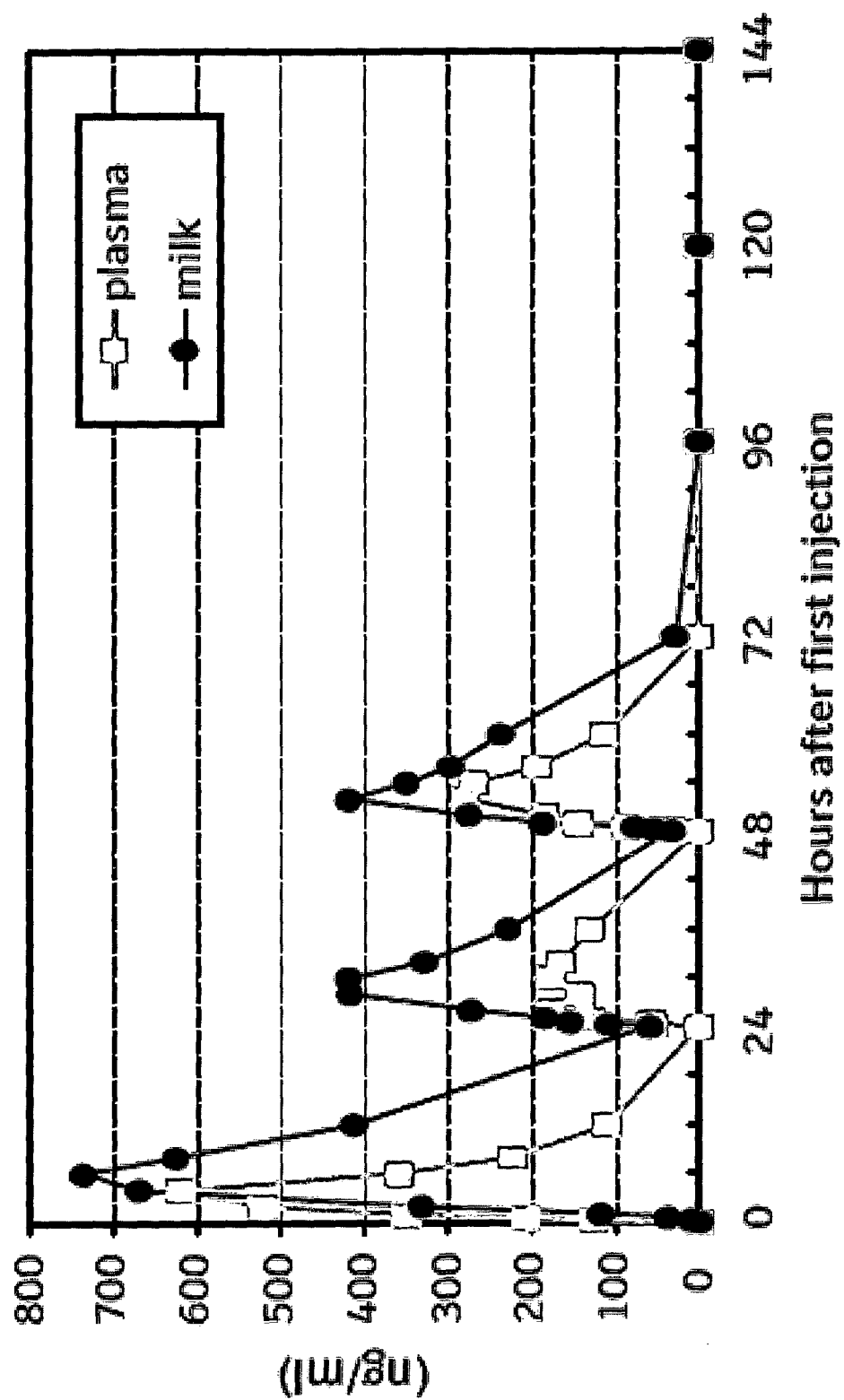
FIG. 1 Mean benzylpenicillin plasma and milk concentrations following intramuscular administration of Mamyzin.

A number of formulations exemplifying the present invention are given below.

EXAMPLE 1

Exemplification Formulations According to the Present Invention, all Percentages in Example 1 are % w/w

| | g | % |
|---|---|---|
| OT11PNTRTU-a | | |
| Penthemate Hydriodide | 5.0 | 31.3 |
| Span 80 | 0.080 | 0.50 |
| Propyl parabens | 0.003 | 0.02 |
| Methyl parabens | 0.013 | 0.08 |
| Ethyl Oleate | 3.271 | 20.45 |
| Sesame oil | 7.63 | 47.71 |
| total | 16.00 | 100.0% |
| OT11PNTRTU-b | | |
| Penthemate Hydriodide | 5.0 | 31.3 |
| Span 80 | 0.080 | 0.50 |
| Propyl parabens | 0.003 | 0.02 |
| Methyl parabens | 0.013 | 0.08 |
| Sesame Oil | 10.90 | 68.15 |
| total | 16.00 | 100.0% |
| OT11PNTRTU-c | | |
| Penthemate Hydriodide | 5.0 | 31.3 |
| PEG12Oleate | 0.048 | 0.30 |
| Propyl parabens | 0.003 | 0.02 |
| Methyl parabens | 0.013 | 0.08 |
| Aerosil R972 | 0.160 | 1.00 |
| Miglyol 812 | 10.78 | 67.35 |
| total | 16.00 | 100.0% |
| OT11PNTRTU-d | | |
| Penthemate Hydriodide | 5.0 | 33.3 |
| PEG12Oleate | 0.075 | 0.50 |
| Propyl parabens | 0.003 | 0.02 |
| Methyl parabens | 0.012 | 0.08 |

| | g | % |
|---|---|---|
| Ethyl Oleate | 9.91 | 66.07 |
| total OTPNTRTU-e | 15.00 | 100.0% |
| Penthemate Hydriodide | 5.0 | 35.0 |
| Tween 80 | 0.022 | 0.15 |
| Ethyloleate | 9.28 | 64.89 |
| total OTPNTRTU-f | 14.30 | 100.0% |
| Penthemate Hydriodide | 5.0 | 34.96 |
| Span 80 | 0.022 | 0.15 |
| Ethyloleate | 9.28 | 64.89 |
| total OTPNTRTU-g | 14.30 | 100.0% |
| Penethamate Hydriodide | 5.0 | 35.0 |
| Tween 80 | 0.022 | 0.15 |
| Span 80 | 0.022 | 0.15 |
| Ethyloleate | 9.26 | 64.74 |
| total OTPNTRTU-h | 14.30 | 100.0% |
| Penethamate Hydriodide | 5.0 | 35.0 |
| Span 80 | 1.430 | 10.00 |
| Ethyloleate | 7.87 | 55.03 |
| total OTPNTRTU-i | 14.30 | 100.0% |
| Penethamate Hydriodide | 5.0 | 35.0 |
| Tween 80 | 0.143 | 1.00 |
| Ethyloleate | 9.16 | 64.0 |
| total OTPNTRTU-j | 14.30 | 100.0% |
| Penethamate Hydriodide | 5.0 | 35.0 |
| Tween 80 | 1.430 | 10.0 |
| Ethyloleate | 7.87 | 55.0 |
| total OTPNTRTU-k | 14.30 | 100.0% |
| Penethamate Hydriodide | 5.0 | 35.0 |
| Ethyloleate | 9.30 | 65.0 |
| total OT11PNTRTU-l | 14.30 | 100.0% |
| Penthemate Hydriodide | 5.0 | 22.7 |
| Tween 80 | 0.110 | 0.50 |
| Propyl parabens | 0.004 | 0.02 |
| Methyl parabens | 0.018 | 0.08 |
| Propylene Glycol | 16.87 | 76.67 |
| total OT11PNTRTU-m | 22.00 | 100.0% |
| Penthemate Hydriodide | 5.0 | 31.3 |
| Span 80 | 0.080 | 0.50 |
| Propyl parabens | 0.003 | 0.02 |
| Methyl parabens | 0.013 | 0.08 |
| Miglyol 840 | 10.90 | 68.15 |
| total OT11PNTRTU-n | 16.00 | 100.0% |
| Penthemate Hydriodide | 5.0 | 22.7 |
| Tween 80 | 0.077 | 0.35 |
| Span 80 | 0.033 | 0.15 |
| Propyl parabens | 0.004 | 0.02 |
| Methyl parabens | 0.018 | 0.08 |

| | g | % |
|---|---|---|
| Ethyl Oleate | 16.87 | 76.67 |
| total OT12PNTRTU-q | 22.00 | 100.0% |
| Penthemate Hydriodide | 5 | 20.5 |
| Benzyl Alcohol | 0.2443 | 1 |
| Tween 80 | 1.222 | 5.00 |
| Span 80 | 0.024 | 0.10 |
| Triacetin | 17.94 | 73.43 |
| total OT12PNTRTU-r | 24.43 | 100% |
| Penthemate Hydriodide | 5.0 | 23.9 |
| Benzyl alcohol | 0.20 | 1.0 |
| Tween 80 | 0.073 | 0.35 |
| Span 80 | 0.031 | 0.15 |
| Lipoid 90H | 0.076 | 0.36 |
| Miglyol 812 | 15.50 | 74.23 |
| total OT12PNTRTU-s | 20.88 | 100% |
| Penthemate Hydriodide | 5.0 | 24.4 |
| Benzyl alcohol | 0.2 | 1.0 |
| Tween 80 | 0.072 | 0.35 |
| Span 80 | 0.031 | 0.15 |
| Ethyl Oleate | 12.1 | 59.0 |
| Triacetin | 3.1 | 15.1 |
| total OT12PNTRTU-t | 20.503 | 100.0% |
| Penthemate Hydriodide | 3.4 | 34.00 |
| Benzyl alcohol | 0.1 | 1.00 |
| Polysorbate 80 | 0.01 | 0.10 |
| Lecithin (phospolipon 90 H) | 0.036 | 0.36 |
| Triacetin | 6.454 | 64.54 |
| total | 10.0 | 100.0% |

EXAMPLE 2

Exemplification of Short Withhold Period

Figure 3:
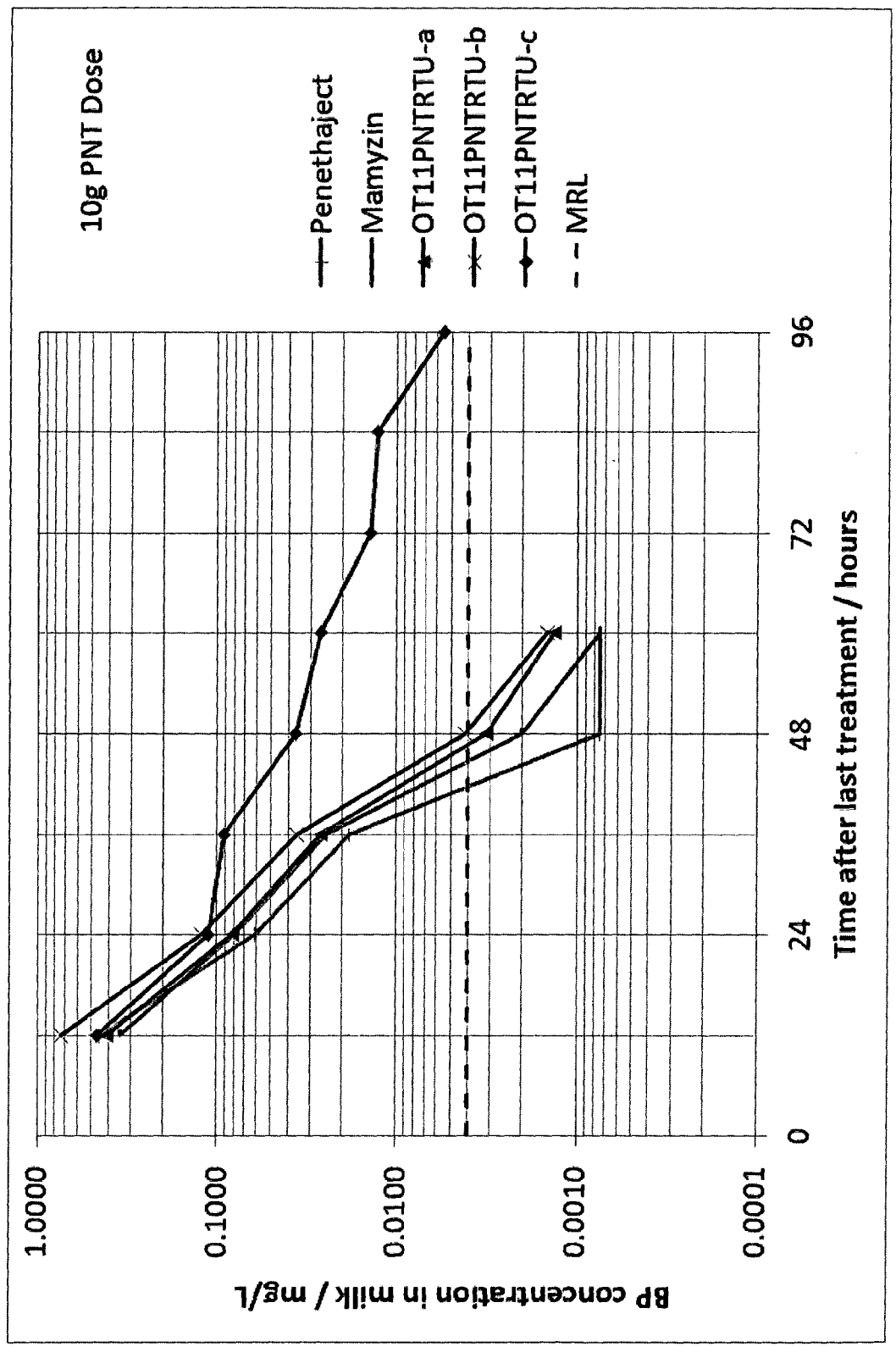
FIG. 3 Benzylpenicillin milk concentrations following intramuscular administration of different PNT compositions.

Surprisingly it was found that by controlling the viscosity of the compositions OT11PNTRTU-a and -b, the drug release from the compositions at the site of injection is fast enough in order to achieve a WHP in milk of equal or smaller than 60 hours, or considering confidence intervals as requested from regulatory authorities up to 72 hours, as shown in FIG. 3.

Figure 2:
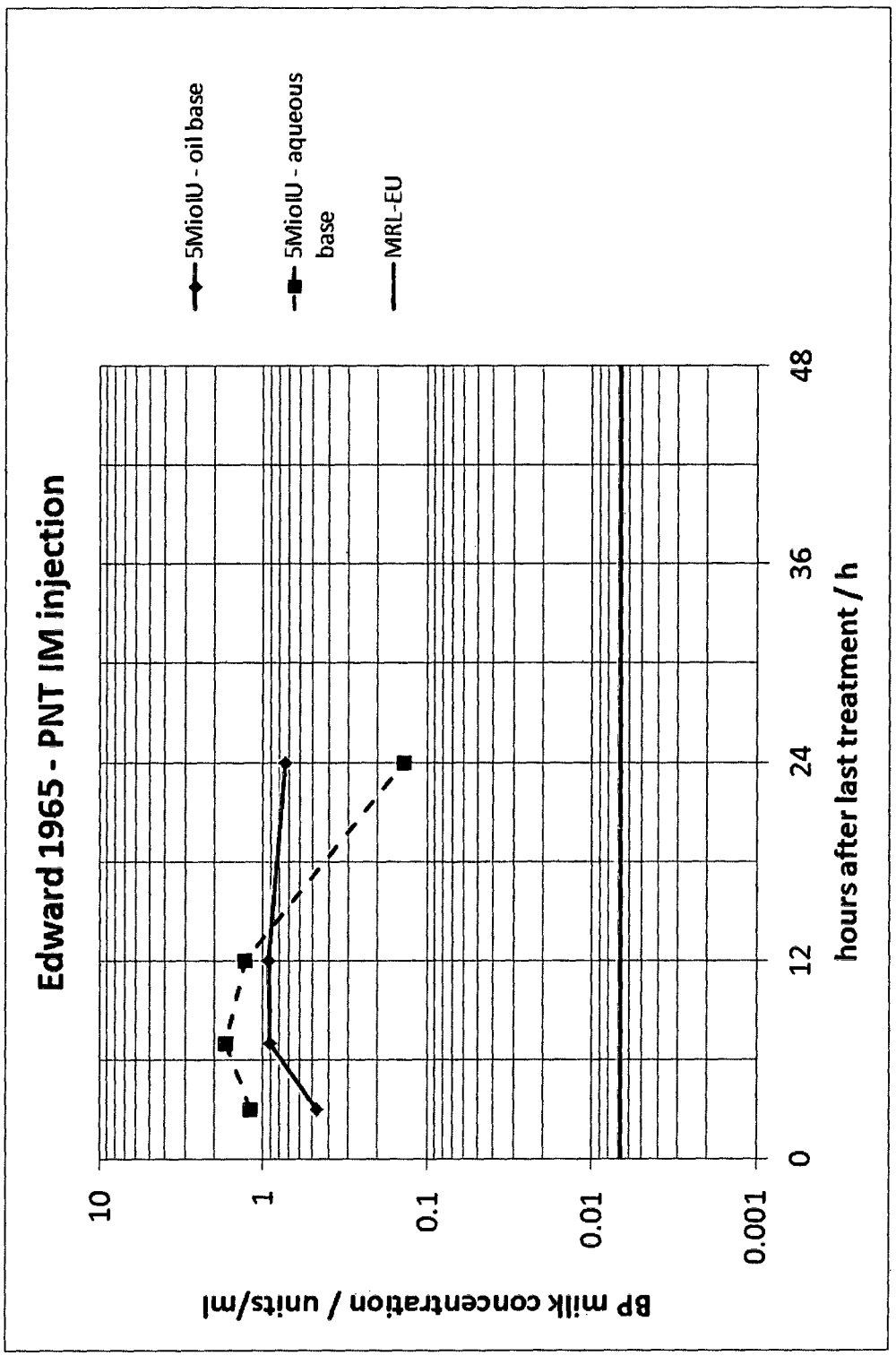
FIG. 2 Benzylpenicillin milk concentrations following intramuscular administration of PNT from Edwards 1965.

Both compositions were given as a 10 g PNT dose. WHP (withhold period) is here defined as when the concentration curve cuts the MRL line followed by the next multiple of 12. For instance a calculated WHP of 52 hours would provide a registered WHP of 60 hours. This also includes that some registration authorities around the world require a consideration of a confidence interval for determination of WHP. These results are especially surprising if one compares the results shown in FIG. 3 with the data from Edwards, S. J. (1964), The Veterinary Record, Vol. 78, No. 17, 583-5, as shown in FIG. 2 for 5 MioIU (equivalent to 5 g PNT) oil based formulation.

The Edwards data would should suggest a much longer WHP than 84 hours with only half the dose (5 g PNT). The composition of the oily vehicle used by Edwards was not disclosed in the published document, however the findings of Edwards is consistent with the general knowledge of oil based vehicles, that the release of active is expected to be slower.

The absorption rate of PNT is a crucial component for a treatment of mastitis in lactating cows. Oil based compositions as injectables are generally regarded as slow release dosage forms. In general, the absorption rate of injectable compositions is fast for aqueous solutions containing a drug with hydrophilic properties and slow for oily solutions containing a drug with lipophilic properties. A prediction of the absorption rate of a drug from an oily suspension is usually based on the properties of the drug.

Figure 4:
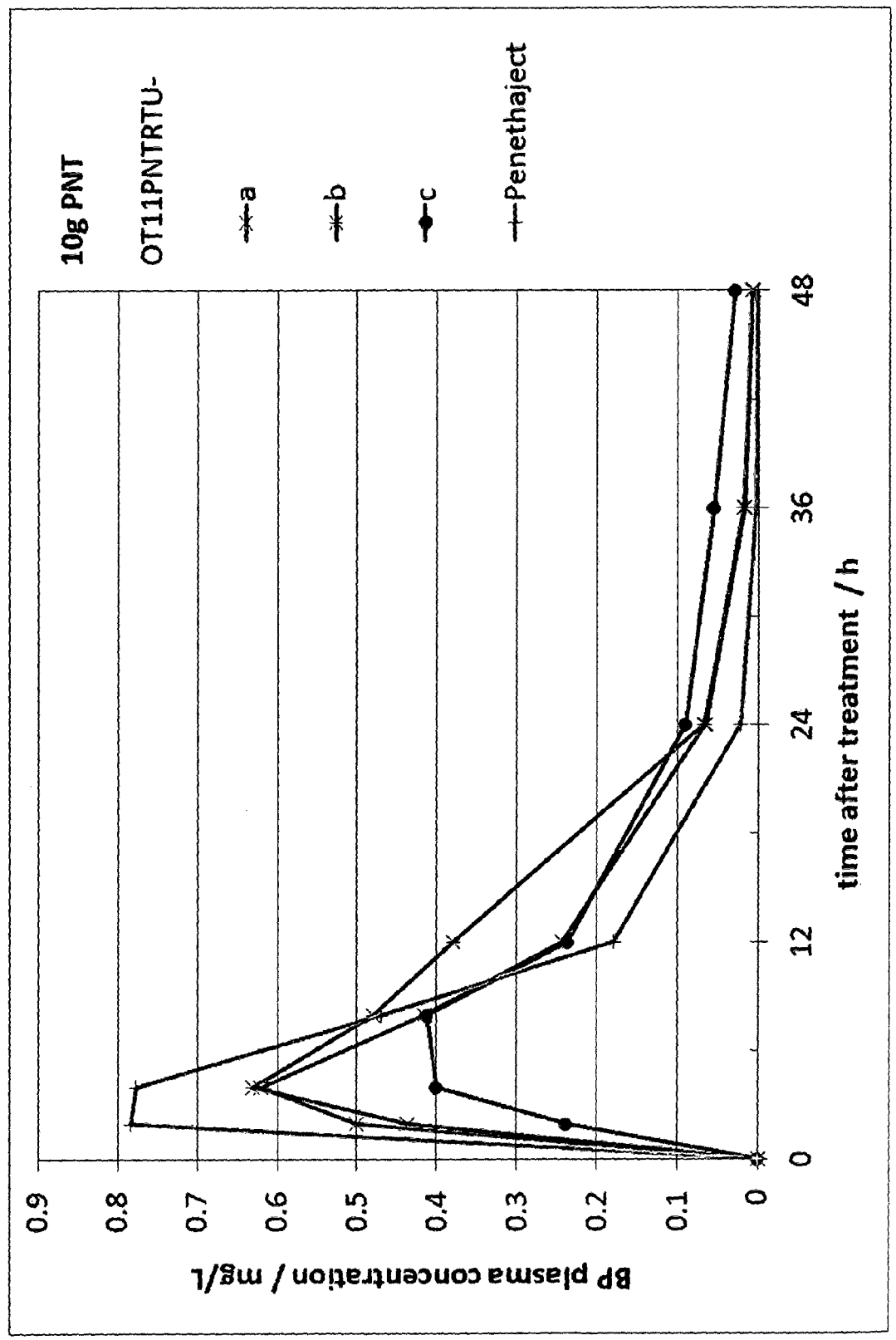
FIG. 4 Benzylpenicillin plasma concentrations following intramuscular administration of different PNT compositions.

The composition of OT11PNTRTU-c with a much higher viscosity compared to OT11PNTRTU-a and -b, has a WHP longer than 96 hours. Table 1 lists the viscosities of the compositions tested. FIG. 4 shows that OT11PNTRTU-c is more slowly absorbed into blood after a 10 g PNT dose compared to all other compositions in FIG. 4 and has still elevated concentrations at 36 hours and 48 hours of BP in plasma after the last treatment, leading to a longer WHP compared to the other compositions.

TABLE 1

Viscosity of test compositions -a, -b, -c, and Penethaject

| Composition | Viscosity mPas at 20° C., Shear rate 1/s |
|---|---|
| Penethaject | 280 |
| OT11PNTRTU-a | 380 |
| OT11PNTRTU-b | 770 |
| OT11PNTRTU-c | 3270 |

It is expected that the PNT compositions disclosed in U.S. Pat. No. 4,446,144 as examples 51 to 53 would also have a similarly slow release and long withhold period, due to the substantial amount of thickener, in the form of 12-hydroxystearin and aluminium monostearate.

Figure 5:
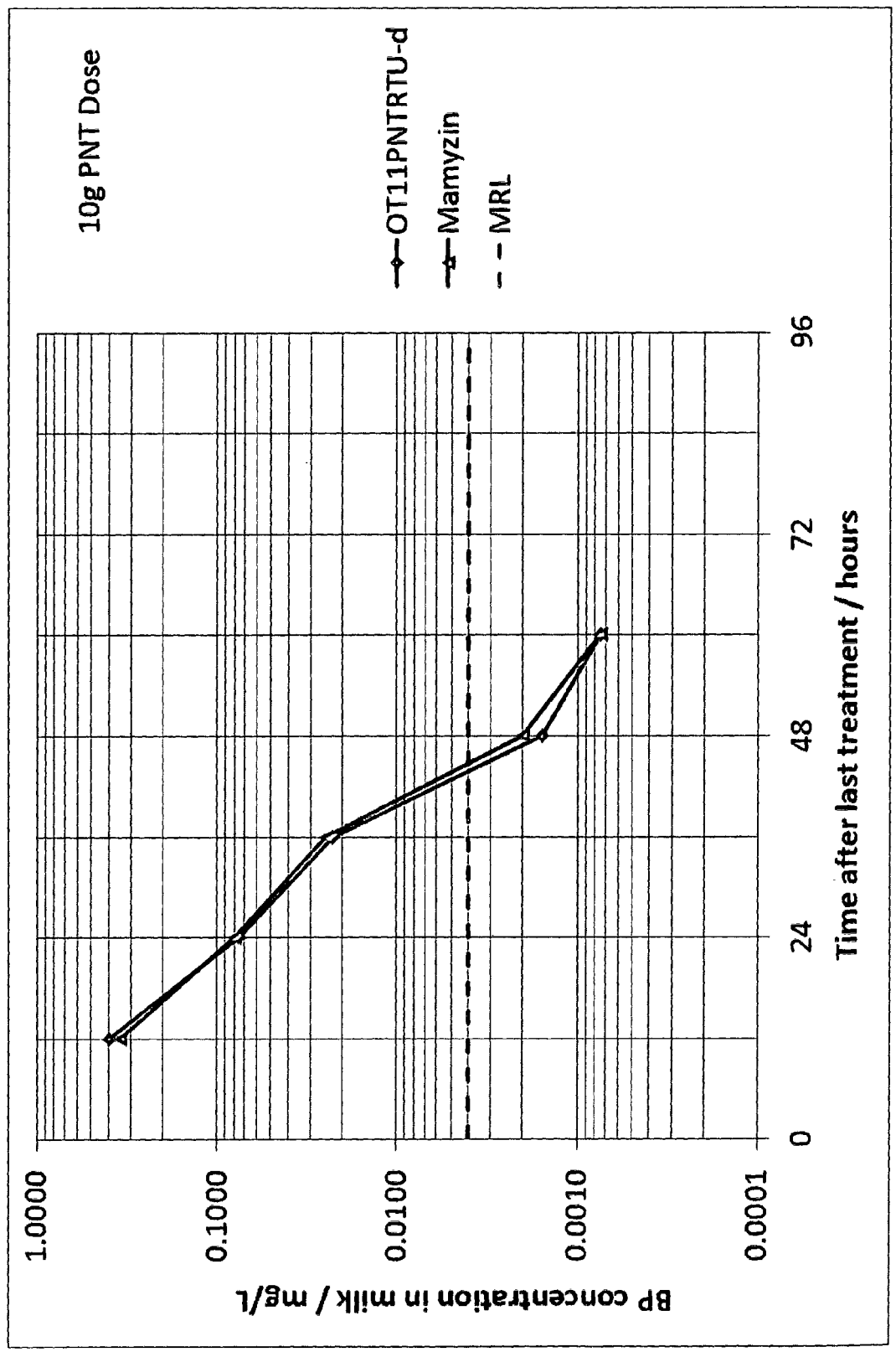
FIG. 5 Benzylpenicillin milk concentrations following intramuscular administration of Mamyzin and composition OT11PNTRTU-d.

Further it was found for a 10 g PNT dose that the WHP in milk of the oil based composition OT11PNTRTU-d is almost identical to the aqueous based Mamyzin™ composition (after reconstitution), as shown in FIG. 5. This is surprising considering that oil based formulations are generally regarded as slow release formulations, and particularly with regard to the lipophilic nature of PNT.

Figure 7:
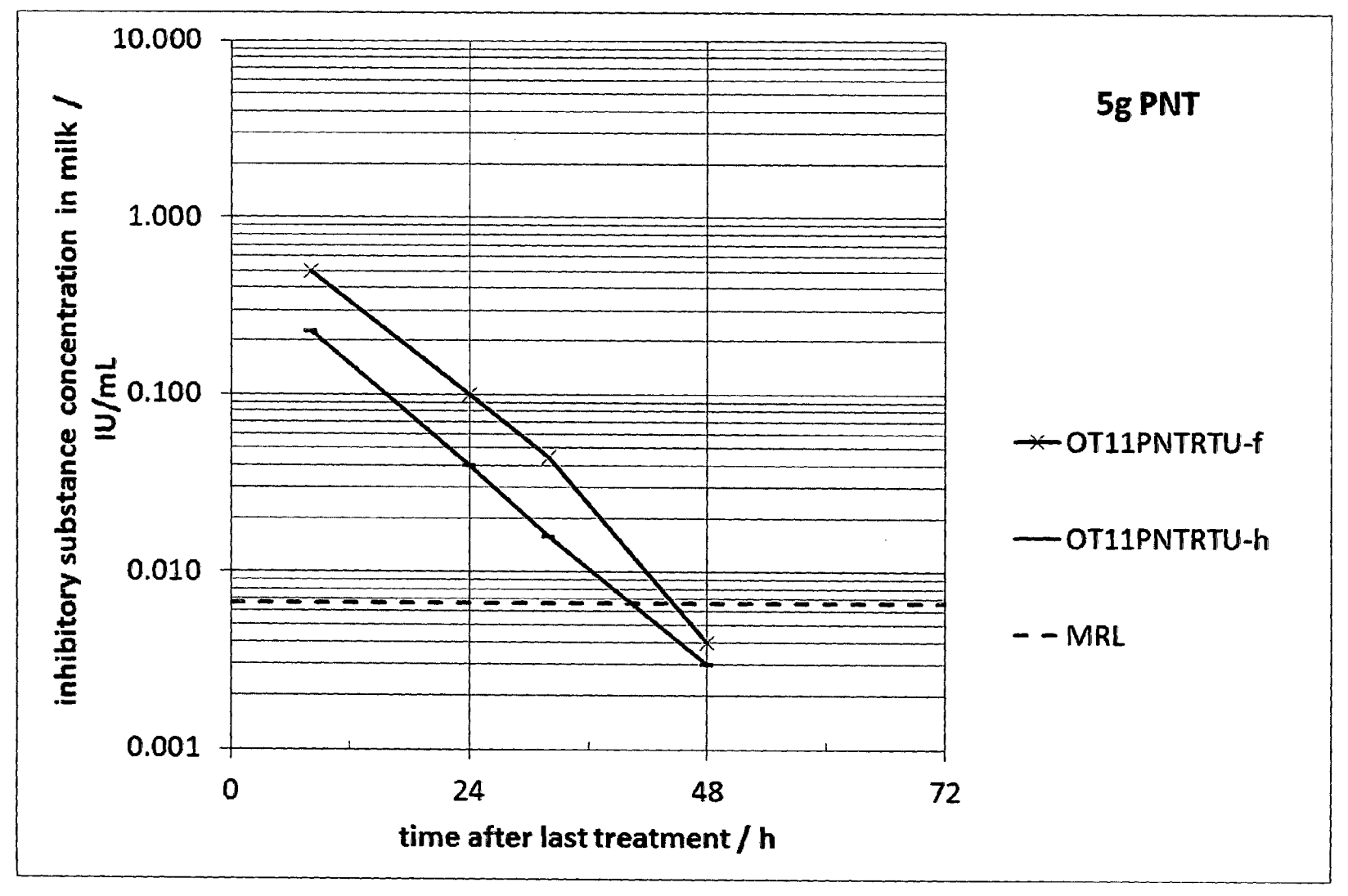
Figure 8:
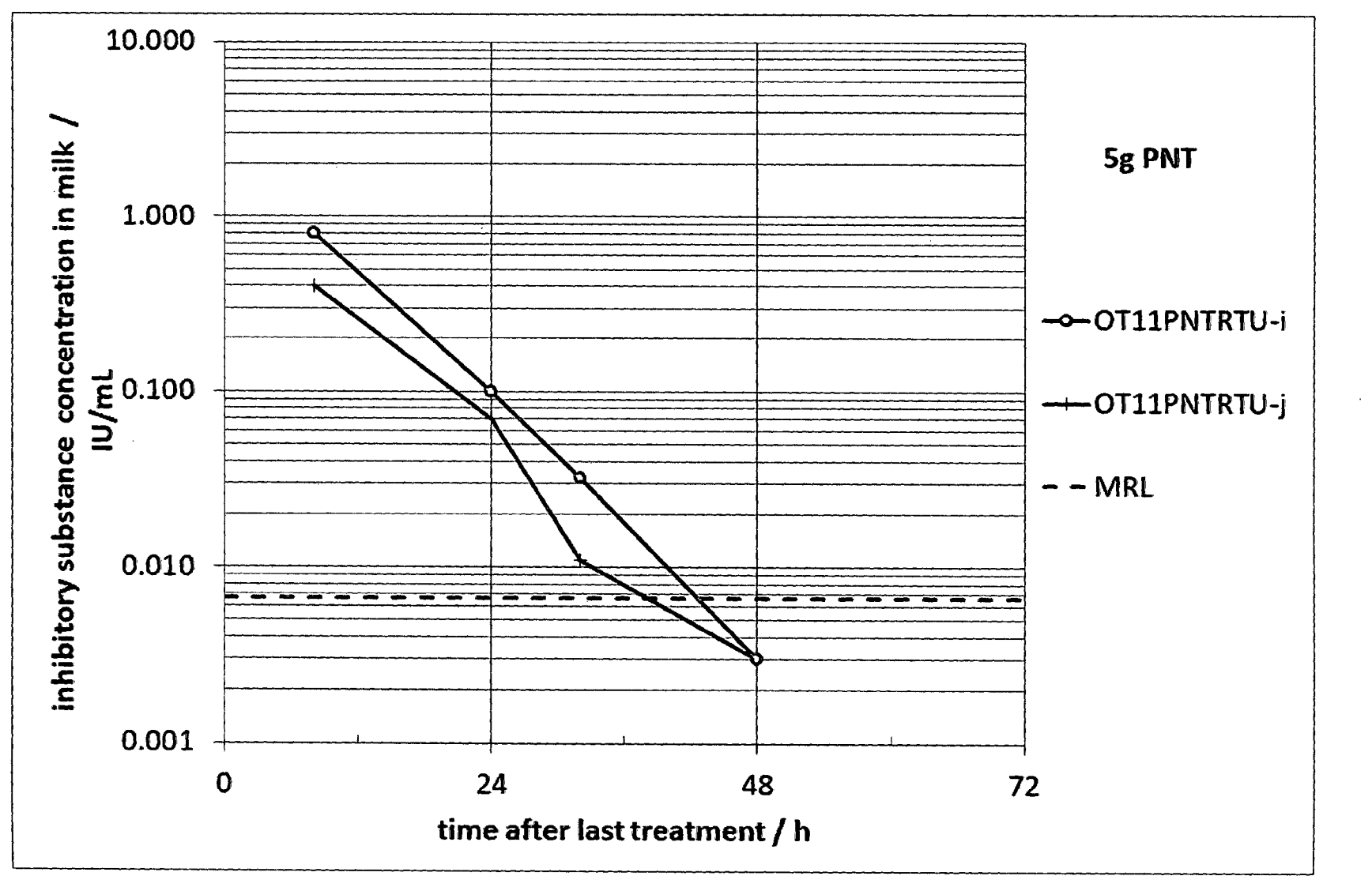

It was also found that with increasing surfactant concentration the WHP can be further decreased. As shown in FIG. 7 a comparison is made between OT11PNTRTU-f that contains 0.15% Span 80, and OT11PNTRTU-h that contains 10% Span 80. Similarly FIG. 8 compares OT11PNTRTU-l that contains 1.00% Tween 80 with OT11PNTRTU-j that contains 10% Tween 80. It is clear that the increase in surfactant corresponds to a decrease in the withhold period.

Figure 9:
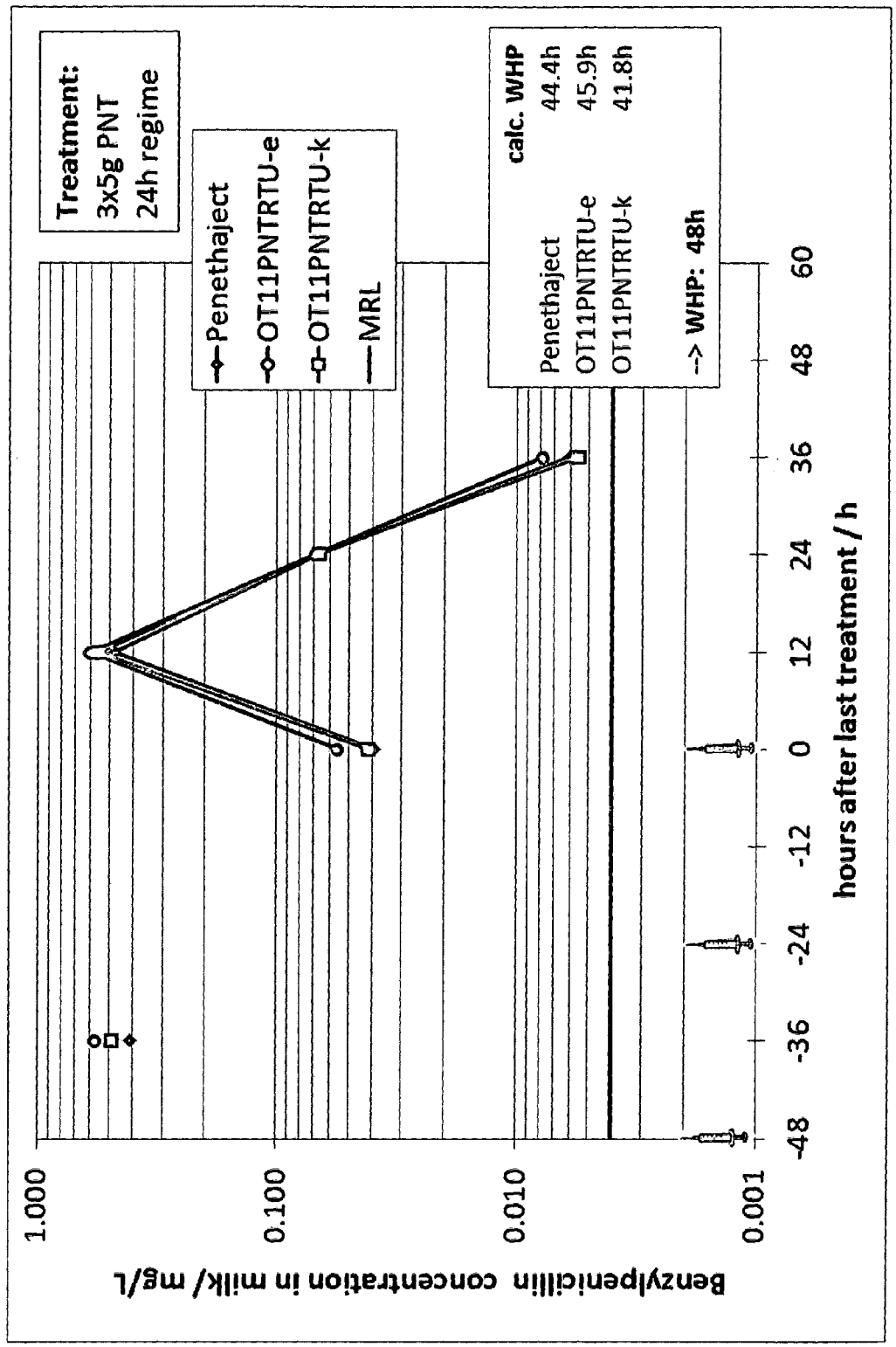
FIG. 9 Benzylpenicillin milk concentration following intramuscular administration of Penethaject and compositions OT11PNTRTU-e, and -k.

FIG. 9 shows the BP concentration in milk for compositions of the present invention over time after three injections (according to a proposed dosage regime), with a comparison between OT11PNTRTU-e, OT11PNTRTU-k and Penethaject™. As can be seen, the calculated WHP following ACVM guidelines of the tested compositions is similar (approximately 42-46 hours) to Penethaject™ as currently available on the market. Surprisingly it was found that this short withhold period is possible for ethyl oleate based composition without any surfactant (OT11PNTRTU-k).

Figure 10:
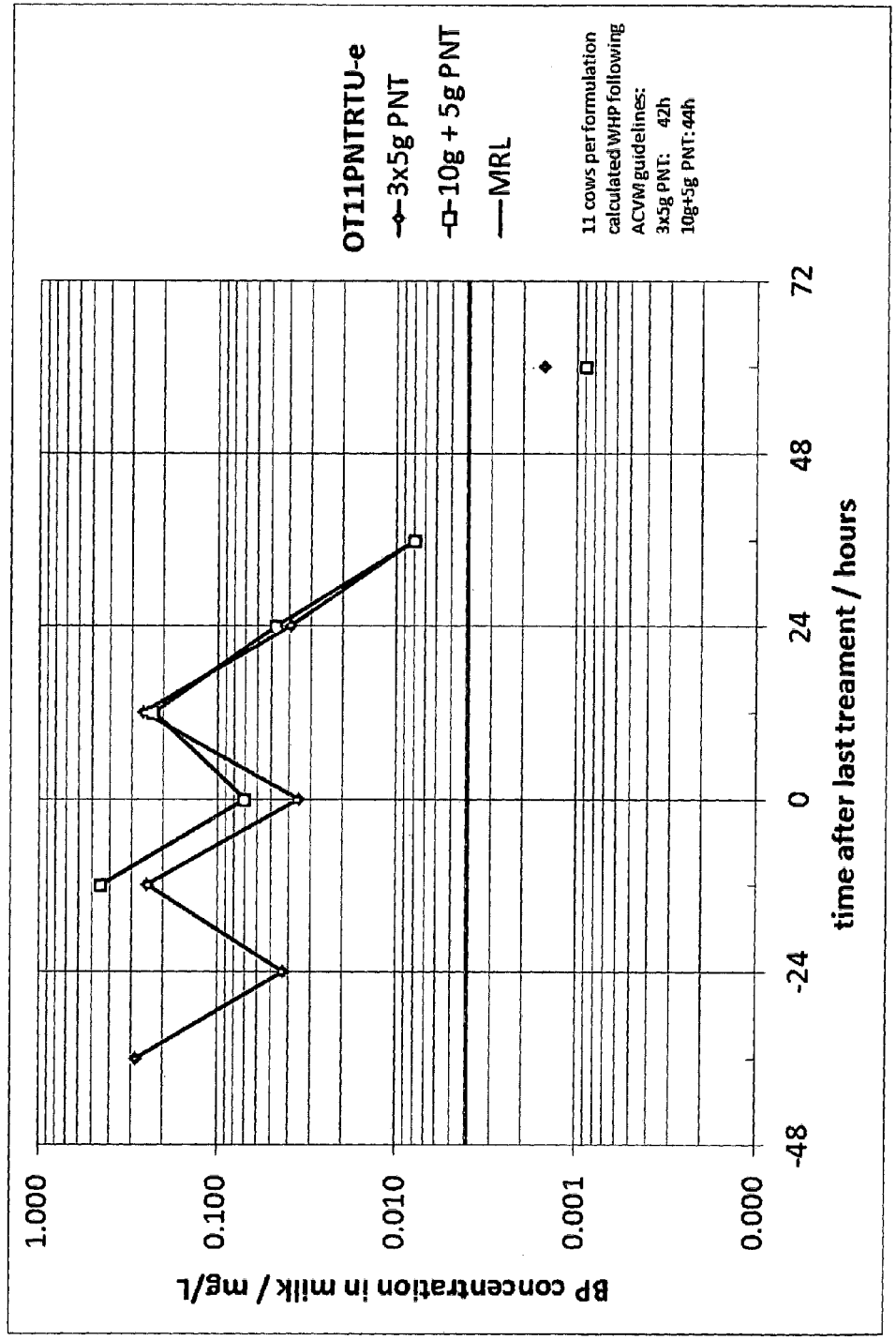
FIG. 10 Benzylpenicillin milk concentration following intramuscular administration of different dosage regimes of composition OT11PNTRTU-e.
Figure 11:
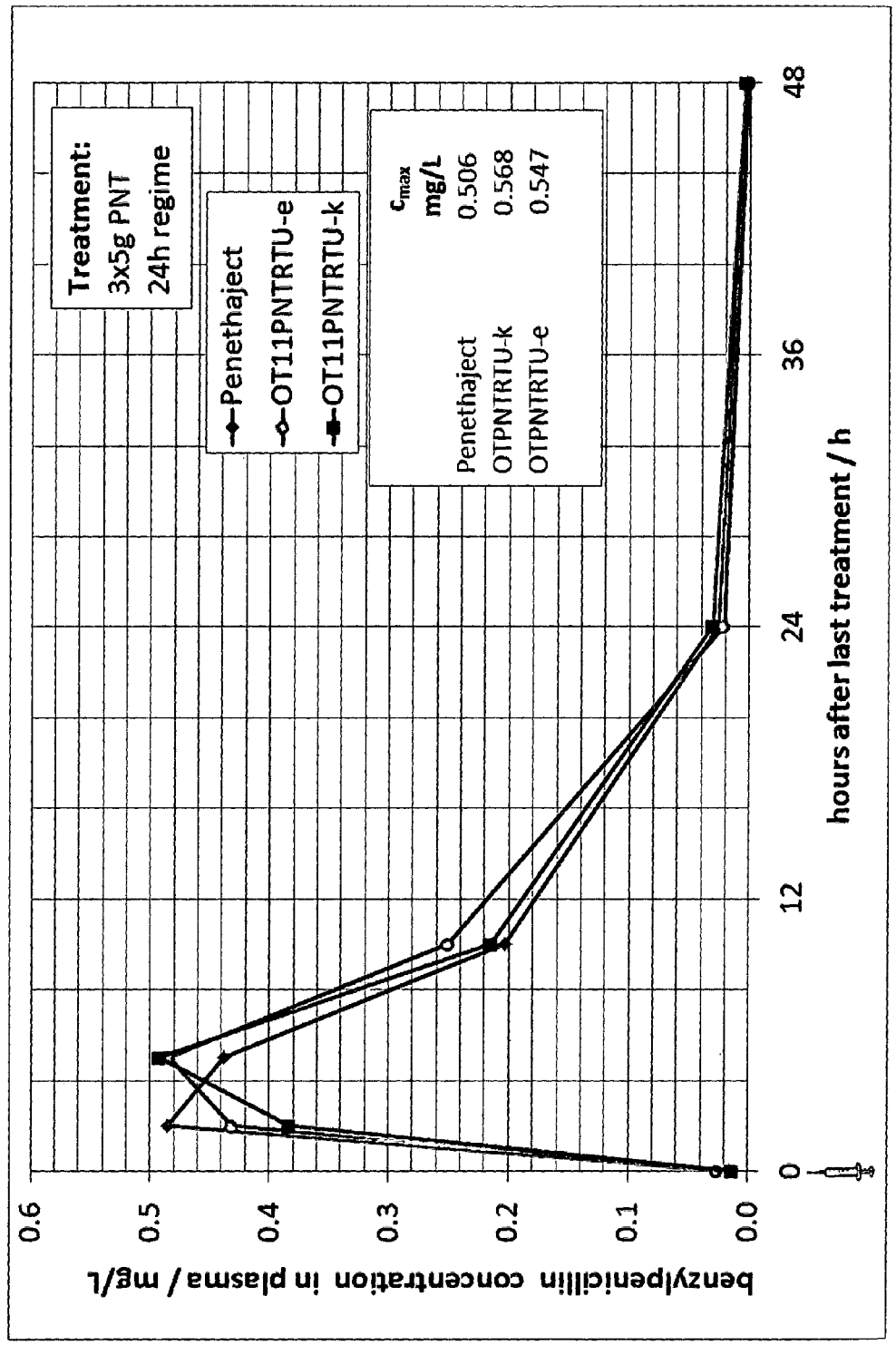
FIG. 11 Benzylpenicillin milk concentration in plasma following intramuscular administration of Penethaject and compositions OT11PNTRTU-e, and -k.
Figure 12:
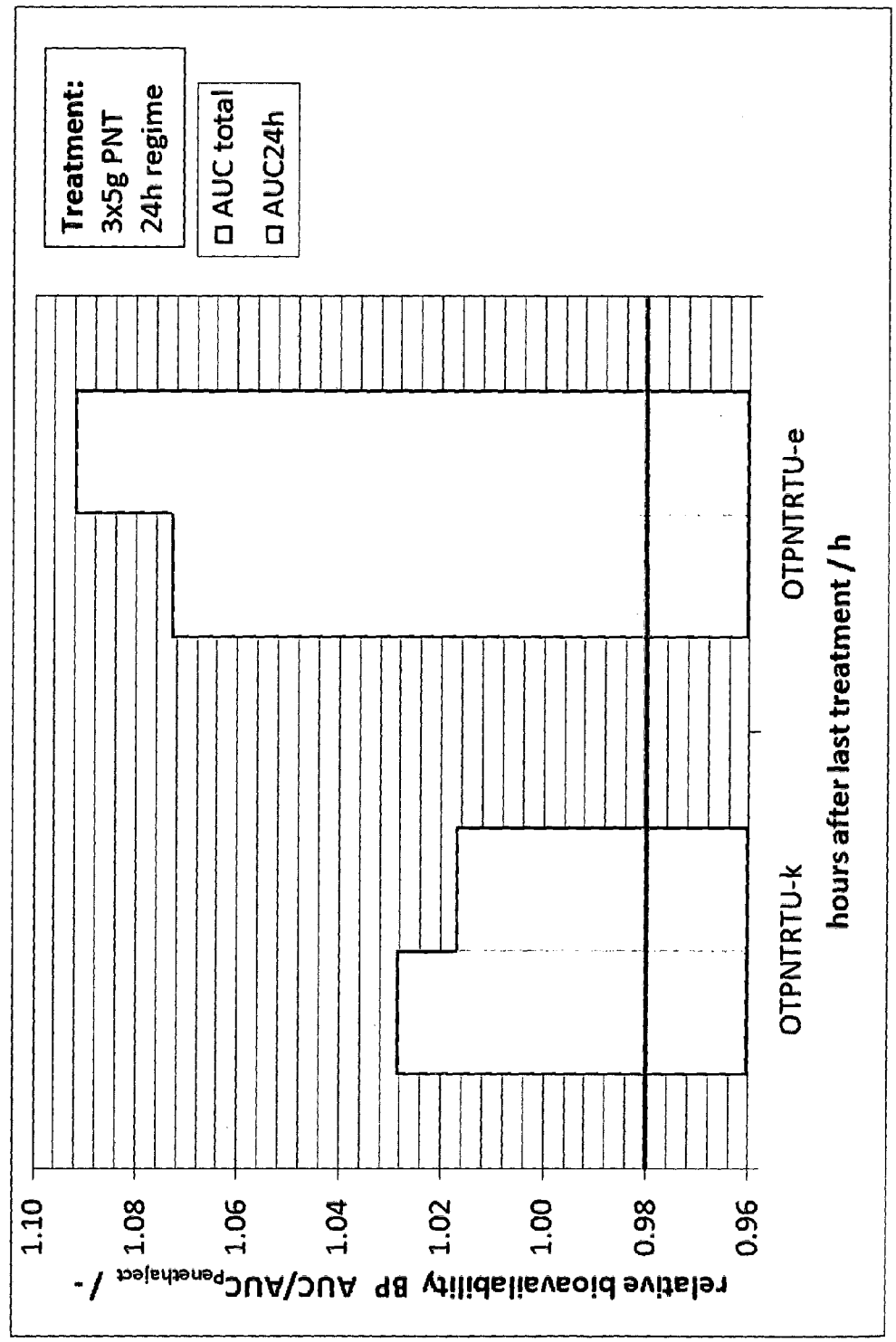
FIG. 12 Relative bioavailability of benzylpenicillin following intramuscular administration of compositions OT11PNTRTU-e, and -k in relation to Penethaject.
Figure 13:
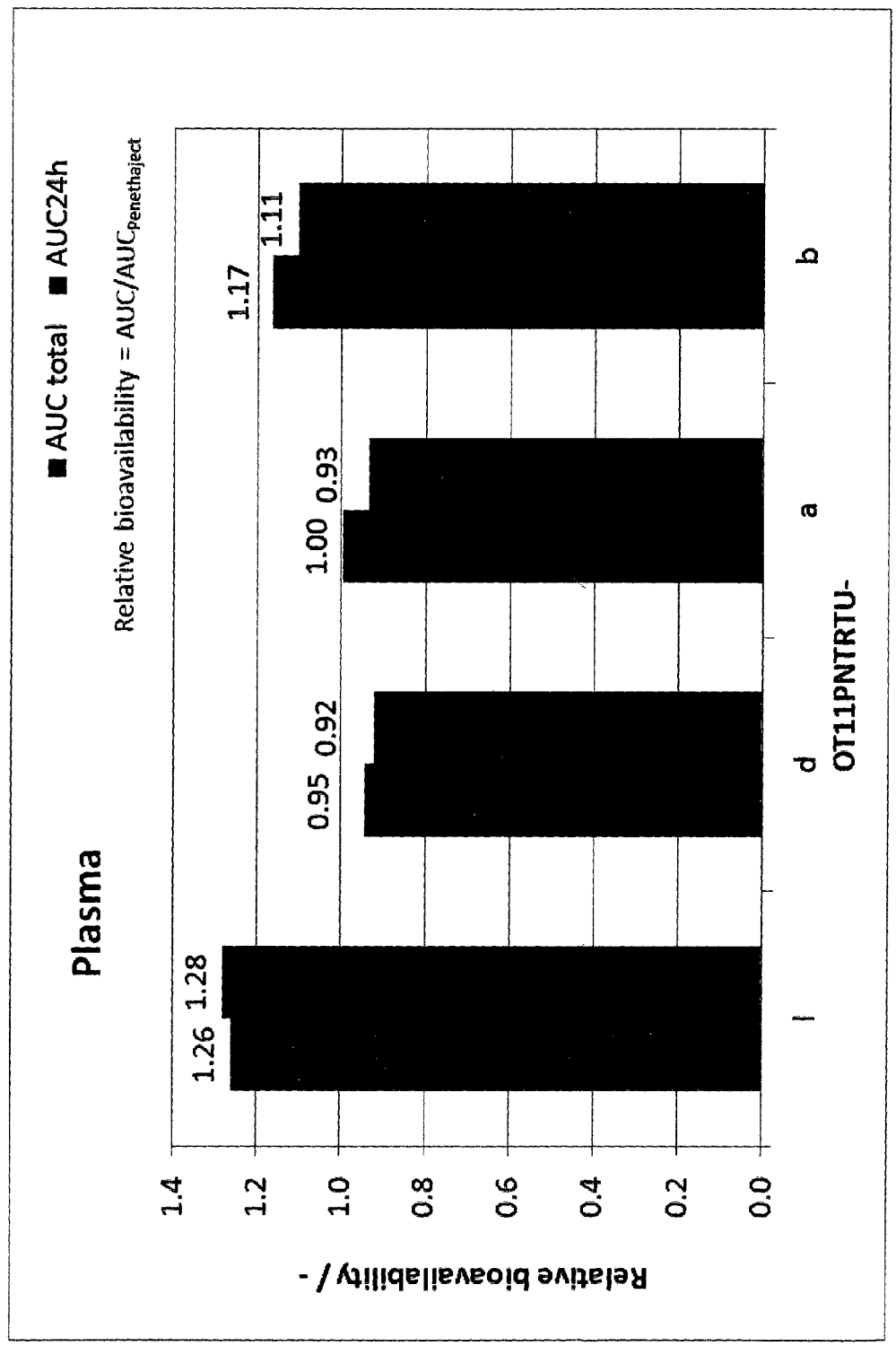
FIG. 13 Relative bioavailability of benzylpenicillin following intramuscular administration of compositions OT11PNTRTU-l, -d, -a and -b in relation to Penethaject.
Figure 14:
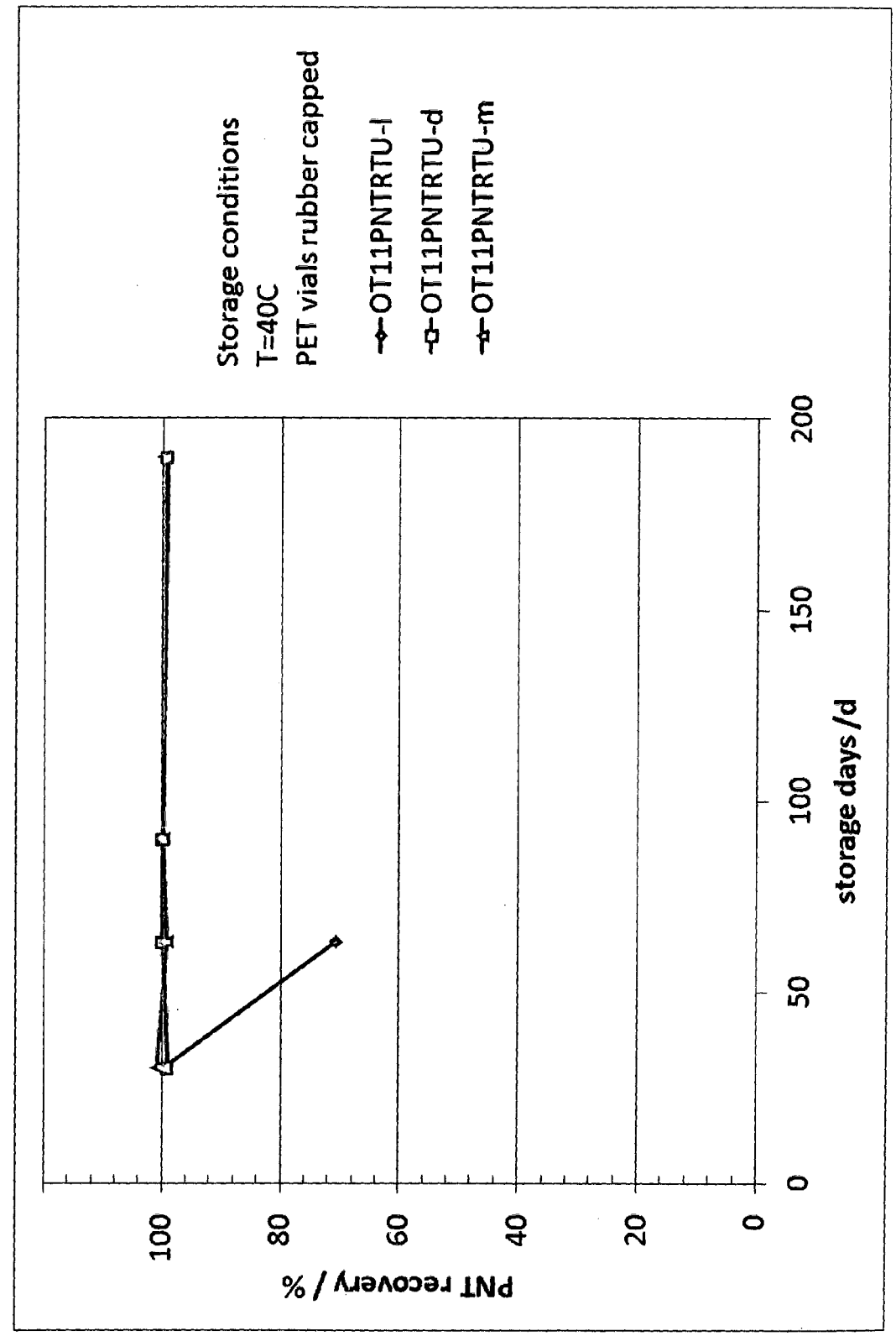
FIG. 14 Recovery percentage of PNT from compositions OT11PNTRTU-l, -d and -n during stability trials.
Figure 15:
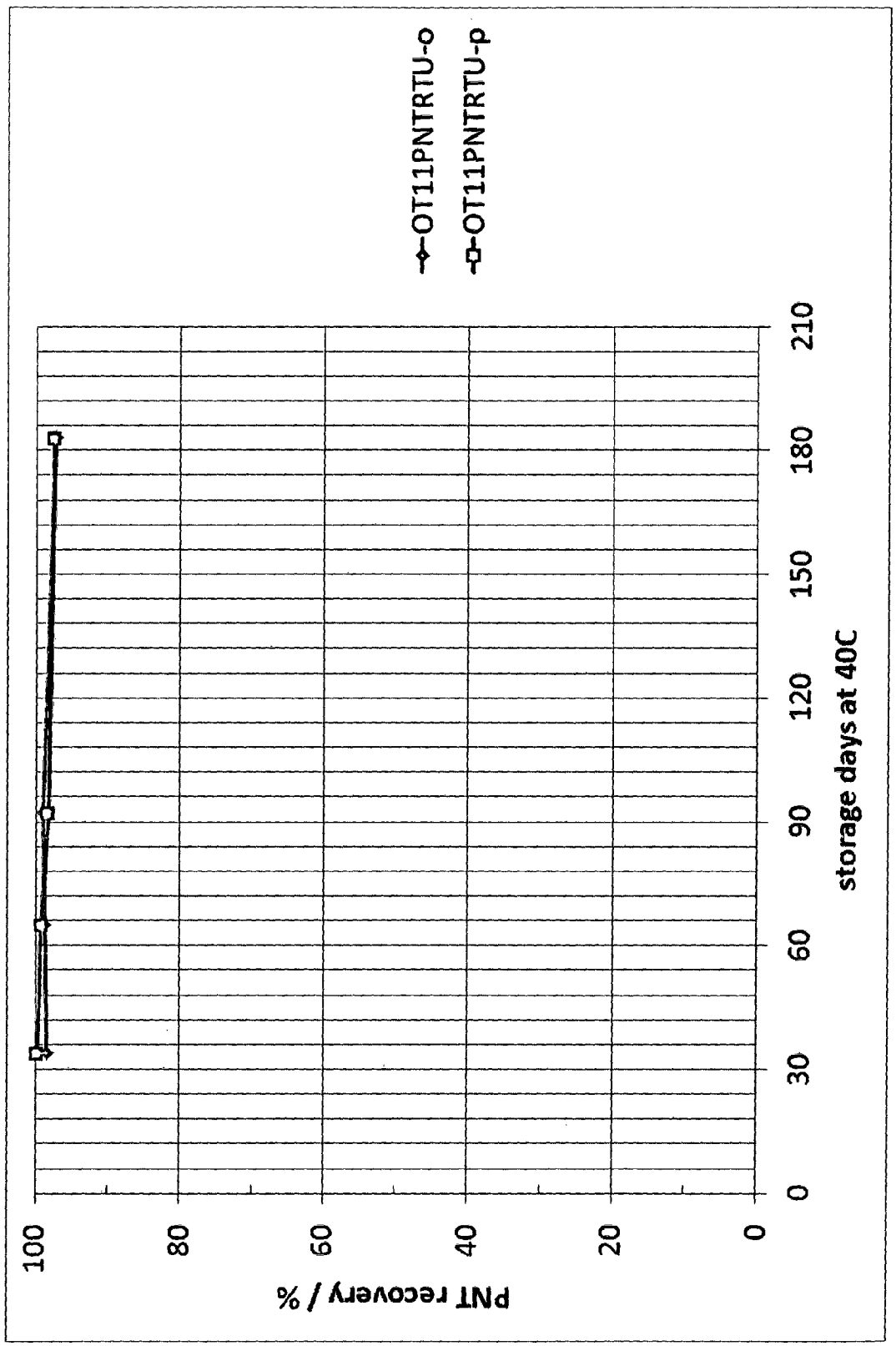
FIG. 15 Recovery percentage of PNT from compositions OT11PNTRTU-o, and -p during stability trials.

Further it was surprisingly found that the calculated WHP for the dosage regimes of 10 g followed by 5 g PNT the next day, and 3×5 g PNT daily doses are both below 48 hours and therefore would have 48 hour WHP following the calculations of New Zealand ACVM guidelines, as shown in FIG. 10. This is surprisingly advantageous to the aqueous suspension Mamyzin™, which following a 10 g+5 g PNT dosage regime has a 60 hour WHP.

EXAMPLE 3

Exemplification of Bioavailability

FIG. 3 shows the BP concentration in milk for various test compositions, Mamyzin™ and Penethaject™ following a 10 g dose of PNT. Again, it can be seen that the compositions OT11PNTRTU-a and -b substantially align with the release profile of Mamyzin™.

Bioequivalence is here defined as when the difference of the area under the curve between the reference product (aqueous based PNT composition) and test product (oil based PNT composition) both given as the same dose (relative bioavailability) is not more than 20% (bioequivalent=1; limits from 0.9 to 1.1) (ACVM REGISTRATION STANDARD AND GUIDELINE FOR THERAPEUTIC EQUIVALENCE OF TRADE NAME PRODUCTS).

FIG. 4 shows the BP concentration in plasma for the compositions OT11PNTRTU-a, -b and -c, as compared to Penethaject™ following a 10 g dose of PNT. Again, it can be seen that the compositions OT11PNTRTU-a and -b substantially align with the release profile of Penethaject™.

The relative bioavailability for the BP plasma results are shown in Table 2. The compositions OT11PNTRTU-a and b meet the requirements of are bioequivalence or even higher bioavailability as defined above, whereas the high viscosity formulation OT11PNTRTU-c shows no bioequivalency.

TABLE 2

Relative bioavailability of test compositions -a, -b, and -c

| Composition | Relative bioavailability $AUC_{24\,h,\,oil}/AUC_{24\,h,\,aq}$ |
|---|---|
| OT11PNTRTU-a | 0.93 |
| OT11PNTRTU-b | 1.11 |
| OT11PNTRTU-c | 0.78 |

The $AUC_{24h}$ of the oil based PNT compositions investigated by Edwards was significantly lower than the aqueous based PNT compositions at equivalent doses, as shown in Table 3. The viscous formulation OT11PNTRTU-c is comparable with the relative bioavailability results of the 5 MioIU oil formulation in Edwards. Although the Edwards data is in milk and FIG. 4 shows data in plasma, it is still appropriate to compare the relative bioavailabilities since there is a direct correlation between plasma and milk BP concentrations in respect to the area under the curve, as shown in FIG. 1.

TABLE 3

Relative bioavailability of Edwards compositions

| Composition | PNT dose Mio IU | $AUC_{24\,h}$ IU/mL*h | Relative bioavailability $AUC_{24\,h,\,oil}/AUC_{24\,h,\,aq}$ |
|---|---|---|---|
| Oil base | 1 | 4.0 | 0.68 |
| Aqueous base | 1 | 5.9 | |
| Oil base | 2 | 5.9 | 0.86 |
| Aqueous base | 2 | 6.9 | |
| Oil base | 5 | 18.2 | 0.77 |
| Aqueous base | 5 | 23.7 | |

Figure 6:
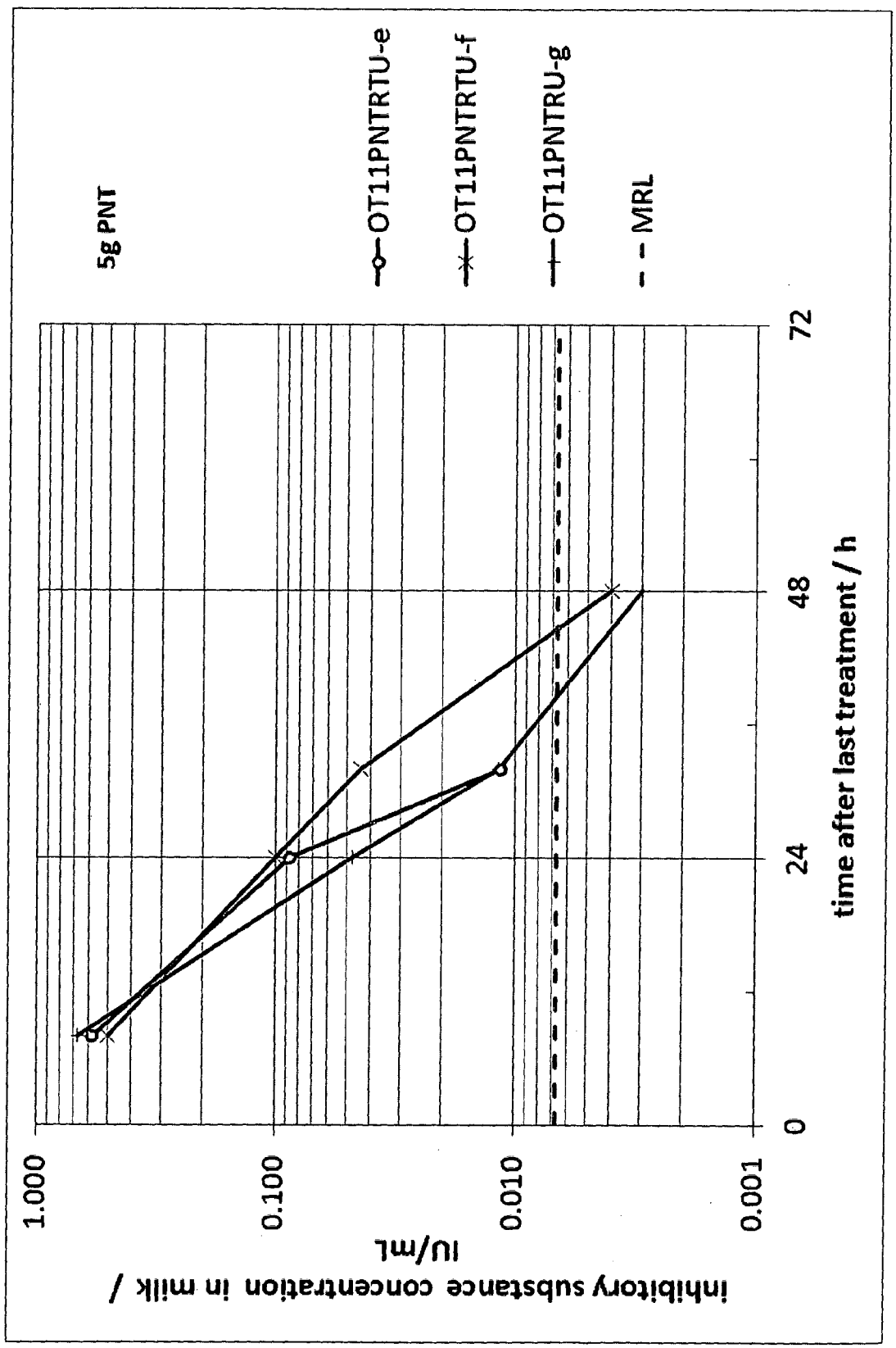
FIG. 6 Inhibitory substance concentration in milk following intramuscular administration of compositions OT11PNTRTU-e, -f, and -g.

Furthermore it was found that different surfactants with different HLB values (Span 80 and Tween 80) or combinations thereof lead to similar BP concentrations in milk (FIG. 6).

It was surprisingly found that when used for a dosage regime of three daily doses of 5 g PNT, the oil based compositions OT11PNTRTU-e and -k have almost the same BP concentrations in milk as the aqueous solution based (when reconstituted) Penethaject™, as shown in FIG. 9.

A further surprising result is that the mean maximum concentration $c_{max}$ of BP in plasma after the last treatment of three daily doses of 5 g PNT for the oil based compositions OT11PNTRTU-e and -k were larger compared to Penethaject, as shown in FIG. 11.

Further it was found that the relative bioavailability of the oil based compositions OT11PNTRTU-e and -k were larger than 1.0, which means that these oil based compositions have a higher bioavailability over 24 hours and overall than Penethaject™, as shown in FIG. 12.

The relative bioavailabilities in plasma of the oil based compositions OT11PNTRTU-l, -d, -a, and -b following a 10 g dose of PNT are shown in FIG. 13. The results demonstrate that the compositions are at least bioequivalent, or have or even higher bioavailability of Penethaject™.

It was very surprisingly to discover that that the bioavailabilities of the oily compositions are higher, or at least meet the lower limit of bioavailability to achieve bioequivalence, compared to an aqueous based PNT composition. Consequently, this also will have a positive impact on BP milk concentrations due to the direct correlation between blood and milk as shown in FIG. 1. This may allow a reduction in the PNT dose whilst still achieving the same bioavailability and efficacy. A reduction in the PNT dose may also lead to a shorter withhold period.

EXAMPLE 4

Exemplification of Storage Stability Characteristics

It was found that PNT is not chemically stable in all non-aqueous formulations despite the assertion made in the patent document U.S. Pat. No. 4,446,144. FIG. 14 shows that PNT in propylene glycol (OT11PNTRTU-l) degrades about 30% w/w after around two months, whereas PNT is chemically stable for about six months in the formulations OT11PNTRTU-d and -m, at a temperature of 40° C. and uncontrolled humidity conditions.

It was further surprisingly found that OT11PNTRTU-d and -n are chemically stable for at least three months at 40° C. and 75% rH even though PNT can hydrolyse in presence of water/moisture. The PNT recovery after two months is shown in Table 4

TABLE 4

Stability of PNT in compositions OT11PNTRTU-d and -n

| Composition | PNT recovery % |
|---|---|
| OT11PNTRTU-d | 100.5 |
| OT11PNTRTU-n | 100.2 |

Glass containers typically deliver the best moisture protection. While PNT powder is stable in PET vials, it is surprising that PNT non-aqueous suspensions are also stable since the diffusion coefficient in liquids are significantly higher compared to powders.

It is evident that the present invention shows very good storage chemical stability of PNT over an extended period of time.

EXAMPLE 5

Exemplification of Physical Stable Non-Aqueous PNT Suspensions

For the treatment of bovine mastitis the PNT concentration in an injectable composition could be 20% w/v or more. While such suspensions of PNT and oil without any further excipients may appear physically stable in controlled laboratory conditions or during storage, under typical transporting and handling the suspensions can show caking behaviour. Initial testing of the sedimentation and/or caking characteristics was performed by subjecting samples to real-world transportation conditions. More controlled and convenient testing was performed using purpose built mechanical agitation apparatus. The controlled laboratory experiments were found to be consistent with the results from the real-world conditions.

It has been found that for some compositions the suspended PNT particles settle on the bottom of the vial or other container, forming a sediment. While it is commonplace for suspensions to settle and form a sediment, to be useful in a practical product such a sediment should be relatively easily re-suspendable, and caking should be avoided. The prior art document U.S. Pat. No. 4,446,144 suggests that vegetable oils should deliver the highest degree of stability. However PNT suspensions in oil vehicles such as sesame oil, such as OT11PNTRTU-b are not re-suspendable by shaking within a practical timeframe.

The time taken to re-suspend caked compositions was over 30 minutes in some cases. Preferably the time taken to re-suspend the settled particles of a composition is in the order of a few minutes at the most. Most preferably if re-suspension is necessary, it should take less than 1 minute.

Accordingly, it is desirable to include an anti-caking agent in the composition of the invention.

To avoid long withhold periods and poor bioavailability, the formulations of the invention use anti-caking agents that do not substantially increase the viscosity of the composition. Without limitation, such non-thickening anti-caking agents include solvents, surfactants and emulsifiers. These agents may have a minor effect on the viscosity of the composition, but it is not significant compared the anti-caking agents colloidal silica and aluminium stearate which are known to be thickeners.

Surfactants such as Tween 80 (polysorbate 80) and PEG12Oleate have been found to provide a more stable suspension, that is more easily re-dispersed.

Surprisingly, it was found that by using a vehicle which has low water solubility such as triacetin, the physical stability of the PNT suspension is dramatically improved during storage and transport. In one trial the composition 100 mL of the PNT suspension OT12PNTRTU-q was contained in a 100 mL PET vial.

A second surprising example is given with OT12PNTRTU-r which is based on a medium chain triglyceride vehicle. The addition of a hydrogenated soybean lecithin to the PNT suspension significantly improved the physical stability.

A preferred composition is OT12PNTRTU-s, which includes triacetin as a vehicle and anti-caking agent, and Tween 80 as an anti-caking agent, along with benzyl alcohol which has also been found to be beneficial to the stability and re-suspendability.

EXAMPLE 6

The preferred formulation is given below:

| Ingredient | Quantity (g/L) | Function |
| --- | --- | --- |
| Penethamate Hydriodide (micronized) | 333.3 g | Active Ingredient |
| Benzyl Alcohol | 10.0 g | Preservative |
| Polysorbate 80 (Tween 80) | 1.0 g | Surfactant |
| Phospholipon H90 (lecithin) | 3.6 g | Emulsifier/Dispersing Agent |
| Triacetin | q.s to 1 L | Vehicle |

In the final formulation, the amount of penethamate (33.33%) is selected to match the concentration of penethamate in the aqueous based pioneer product Mamyzin (when reconstituted). The concentration is very high relative to other injectables, since penethamate requires a reasonably high dose, while there this is a practical minimum to the volume of liquid that can be injected into an animal at one site. This high proportion of suspended solid exacerbates the caking problem, since a large lump of solid cake is more difficult to resuspend than a small amount.

The amount of benzyl alcohol is a standard amount when used as preservative.

The quantities of polysorbate 80 and phospholion H90 are standard amounts, and function to assist with the re-suspension of the active after storage. The triacetin alone overcomes much of the caking problem, but the dispersion and re-suspension is still improved (i.e. faster to re-suspend) with the addition of these agents.

The surfactant (polysorbate 80) also improves the manufacturing process, since it helps the triacetin carrier 'wet' the active much faster, allowing for more rapid dispersion. Without surfactant the active tends to float on top of the liquid carrier, and requires a lot of mixing to disperse it through as a suspension. In a bulk manufacturing process this would be a significant inconvenience.

Further Data

The stability of the final formulation has not yet been completed, but it appears that the shelf-life at room temperature will be at least 12 months.

Stability Trial:

Stability Parameters

| Inspection | Acceptance criteria |
| --- | --- |
| Description | An off-white homogenous suspension. May separate on standing. Resuspends on shaking. |
| Relative Density | 1.000-1.500 g/mL @ 20° C. |
| Penethamate Hydriodide | 29.99-36.66% w/v |
| Sterility | By Direct Inoculation Method (BP) |
| | No growth in Fluid Thioglycollate Medium after 14 days (minimum) incubation at 30-35° C. |
| | No growth in Soybean Casein Digest Medium after 14 days (minimum) incubation at 20-25° C. |

Stability Data:

| | Batch No.: T1958 Packaging: 100 mL clear PET vials | | | | |
| --- | --- | --- | --- | --- | --- |
| Test | Storage conditions | Months | | | |
| | | 0 | 1 | 3 | 6 |
| Description An off-white homogenous suspension | 25° C./60% RH | Complies | — | Complies | Complies |
| | 30° C./65% RH | Complies | — | Complies | Complies |
| | 40° C./75% RH | Complies | Complies | Complies | Complies |
| Relative Density 1.000-1.500 g/mL @ 20° C. | 25° C./60% RH | 1.224 | — | 1.223 | 1.224 |
| | 30° C./65% RH | 1.224 | — | 1.227 | 1.223 |
| | 40° C./75% RH | 1.224 | 1.224 | 1.224 | 1.221 |
| Penethamate Hydriodide 29.99-36.66% w/v | 25° C./60% RH | 33.44 | — | 33.6 | 33.8 |
| | 30° C./65% RH | 33.44 | — | 34.8 | 33.5 |
| | 40° C./75% RH | 33.44 | 33.57 | 34.0 | 32.4 |
| Sterility Direct Inoculation Method | 25° C./60% RH | pass | — | pass | pass |
| | 30° C./65% RH | pass | — | pass | pass |
| | 40° C./75% RH | pass | * | pass | pass |

\* test was not performed;
— test not required

Withhold Time

Figure 16:
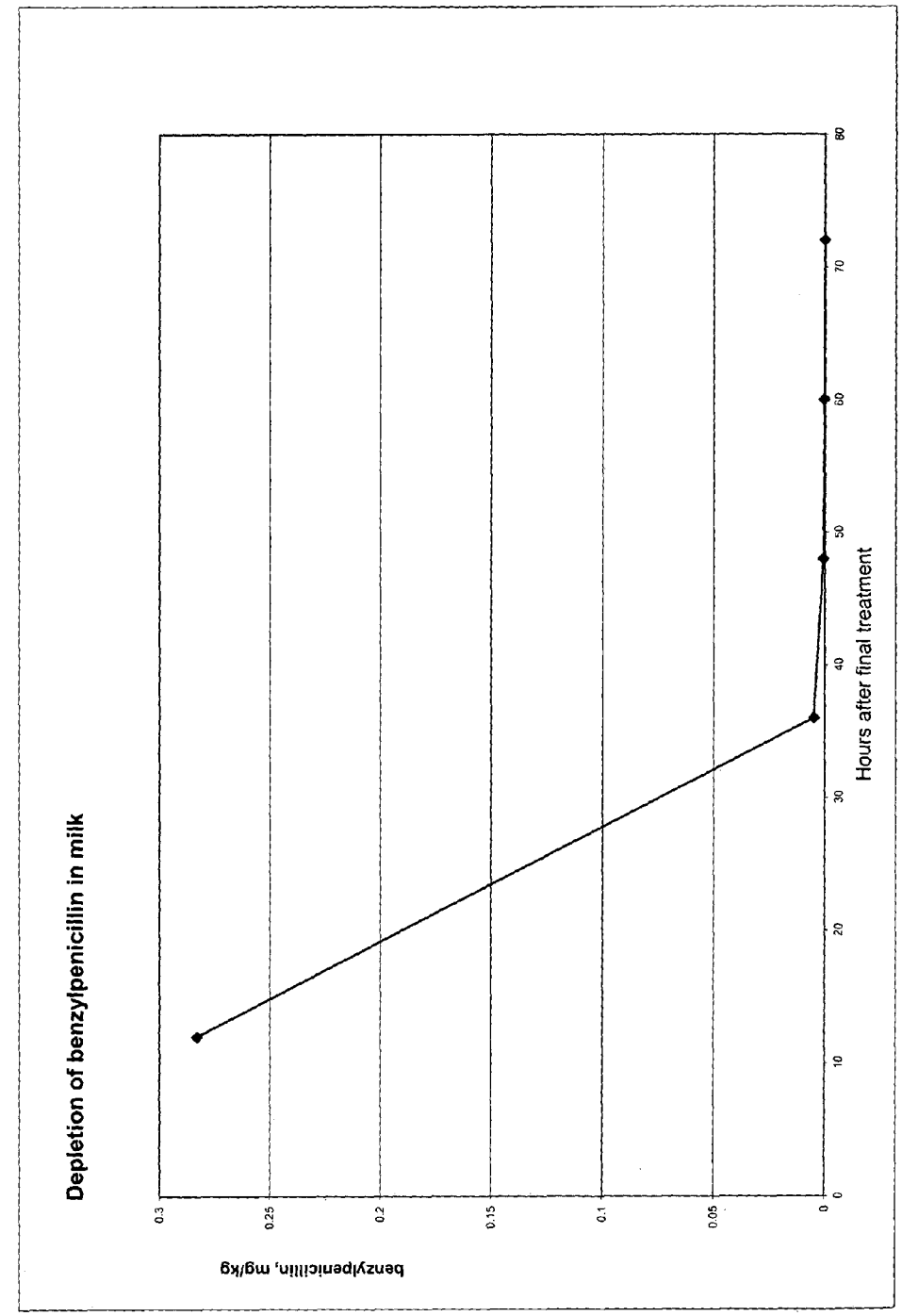
FIG. 16 Depletion of benzyl/penicillin in milk from Example 6

A study was performed to determine the withhold time of the preferred embodiment, namely Example 6. The study used 22 cows in which 5 g (15 mL) of penethamate was injected intramuscularly on three consecutive days. Milk samples were collected from all cows, twice daily, up to 120 hours after the final injection. Milk from the milkings at 12, 36, 48, 60 and 72 hours were analysed for penicillin residues. The results shown in FIG. 16 show that the benzylpenicillin residue in the milk drops below the MRL (maximum reside limit) of 0.004 mg/kg at around 41 hours after the final injection. This would provide a withhold time, based on twice daily milkings, of 48 hours.

This is equivalent to the 48 hour withhold time of the product Mamyzin, which is an aqueous reconstituted suspension.

Bioequivalence

A study was performed to determine the bioequivalence of Example 6 with Mamyzin.

A 2×2 crossover study using 20 dairy heifers was performed. All heifers received a 15 mg/kg intramuscular dose of penethamate hydroiodide on Day 0 and on Day 14, as the formulation in Example 6 or 'Mamyzin'. After a 14 day wash-out period, treatments were reversed. Blood was collected pretreatment, then 1, 2, 3, 4, 5, 6, 9, 12, 18, 24 & 36 hrs after each treatment. Blood was centrifuged and plasma samples were frozen, then dispatched to the laboratory for benzylpenicillin analysis (LC/MS/MS assay). Assay results were used to calculate pharmacokinetic parameters, to investigate bioequivalence. According to the area under the curve (AUC) of the drug concentrations in blood over time, the preferred treatment is bioequivalent to Mamyzin.

The preferred manufacturing process is as follows:

Formulation Process
- Add 56% of Triacetin to a suitably sized manufacturing vessel
- Add Benzyl Alcohol and Polysorbate 80 with mixing
- Filter the mixture through a sterile 0.2 µm filter into sterile tank
- Heat to approximately 55° C., check temperature and maintain the temperature
- Add Phosholipon H90, suspend and homogenise well. Check homogeneity
- Add penethamate hydriodide (micronised, sterile), suspend and homogenise well.

Check Homogeneity
- Cool suspension to approximately 25° C. Check temperature
- Make up to volume with Tracetin.
- Homogenise to homogeneous suspension, check homogeneity This formulation and process has produced a stable non-caking injectable product that works at least as well as conventional PNT treatments.

It has a viscosity of 77 cps@20° C. on Brookfield viscometer with a LV1 spindle at 30 rpm. The density is 1.224 g/cm$^3$ Aspects of the present invention have been described by way of example only and it should be appreciated that modifications and additions may be made thereto without departing from the scope of the appended claims.

The invention claimed is:

1. A composition comprising penethamate (PNT) or a pharmaceutical equivalent thereof; and triacetin.

2. A composition as claimed in claim 1 wherein the viscosity of the composition is less than 3000 mPa·s at a temperature of 20° C. and a shear rate of 1/s, wherein the viscosity is measured with a cup cylinder method.

3. A composition as claimed in claim 1 wherein the composition comprises 55% w/v or less of penethamate (PNT) or a pharmaceutical equivalent thereof.

4. A composition as claimed in claim 3 wherein the composition comprises 15-55% w/v of penethamate (PNT) or a pharmaceutical equivalent thereof.

5. A composition as claimed in claim 4 wherein the composition comprises 20-35% w/v of penethamate (PNT) or a pharmaceutical equivalent thereof.

6. A composition as claimed in claim 1 further comprising at least one anti-caking agent.

7. A composition as claimed in claim 6 wherein the anti-caking agent is non-thickening.

8. A composition as claimed in claim 1 wherein the composition is in liquid form.

9. A composition as claimed in claim 1 comprising penethamate (PNT) having a particle diameter $d_{50}$ of 8-30 microns.

10. A composition as claimed in claim 1 further comprising a surfactant.

11. A composition as claimed in claim 10 wherein the surfactant is polysorbate 80.

12. A composition as claimed in claim 1 further comprising a preservative.

13. A composition as claimed in claim 12 wherein the preservative is benzyl alcohol.

14. A composition as claimed in claim 1 further comprising an emulsifier or dispersing agent.

15. A composition as claimed in claim 14 wherein the emulsifier or dispersing agent is phospholipon H90.

16. A pre-filled syringe comprising a composition as claimed in claim 1.

17. A pre-filled syringe as claimed in claim 16 comprising 5 g of penethamate.

18. A method for the treatment of a microbial infection comprising administering to an animal in need thereof a composition as claimed in claim 1 by intramuscular or subcutaneous injection.

19. A method as claimed in claim 18 wherein the microbial infection is pre-clinical or clinical mastitis.

20. A method as claimed in claim 18 wherein the method of treatment comprises a dosage regime of 5 g penethamate per day repeated for approximately three days.

21. A method of manufacturing the composition as claimed in claim 10 comprising:
   a) mixing triacetin and a surfactant in a container to form a homogenous mixture, and
   b) dispersing the penethamate (PNT) or a pharmaceutical equivalent thereof in the triacetin mixture.

22. A method of manufacturing as claimed in claim 21 further comprising adding a preservative to the triacetin in step a).

23. A method of manufacturing as claimed in claim 21 wherein high shear dispersion equipment is used in step b).

* * * * *